US012725266B2

(12) United States Patent
Sasuga et al.

(10) Patent No.: US 12,725,266 B2
(45) Date of Patent: Sep. 1, 2026

(54) MEDICAL IMAGE PROCESSING APPARATUS, MEDICAL IMAGE PROCESSING METHOD, AND PROGRAM

(71) Applicant: FUJIFILM Corporation, Tokyo (JP)

(72) Inventors: Saeko Sasuga, Tokyo (JP); Rena Kamoda, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 362 days.

(21) Appl. No.: 18/452,568

(22) Filed: Aug. 21, 2023

(65) Prior Publication Data

US 2023/0394672 A1 Dec. 7, 2023

Related U.S. Application Data

(63) Continuation of application No. PCT/JP2022/006046, filed on Feb. 16, 2022.

(30) Foreign Application Priority Data

Feb. 22, 2021 (JP) ................................ 2021-026334

(51) Int. Cl.
*G06T 7/12* (2017.01)
*A61B 6/50* (2024.01)
(Continued)

(52) U.S. Cl.
CPC .............. *G06T 7/12* (2017.01); *G06T 7/0012* (2013.01); *G06T 7/73* (2017.01); *G06T 15/08* (2013.01);
(Continued)

(58) Field of Classification Search
CPC ........... G06T 7/12; G06T 7/73; G06T 7/0012; G06T 15/08; G06T 15/20; G06T 2200/04;
(Continued)

(56) References Cited

U.S. PATENT DOCUMENTS

2012/0209103 A1 8/2012 Sakuragi
2016/0143697 A1* 5/2016 Chen ...................... G06F 17/17 703/2

(Continued)

FOREIGN PATENT DOCUMENTS

JP H10309281 11/1998
JP 2009022369 2/2009

(Continued)

OTHER PUBLICATIONS

Marshall, D. F., Gardner, H. J., & Thomas, B. H. (Jan. 2015). Interactive visualisation for surface proximity monitoring. In Proceedings of the 16th Australasian User Interface Conference (AUIC 2015) (vol. 27, p. 30) (Year: 2015).*

(Continued)

*Primary Examiner* — Utpal D Shah
*Assistant Examiner* — Jack Peter Kraynak
(74) *Attorney, Agent, or Firm* — JCIPRNET

(57) ABSTRACT

Provided are a medical image processing apparatus, a method, and a program capable of supporting determination of a separation plane based on a three-dimensional distance between tissue to be resected and tissue to be preserved. A processor executes a command of the program to acquire a three-dimensional medical image, set a separation plane for separating a first region specified in the medical image, measure a first distance which is a nearest neighbor distance between any position on a surface of the first region and the separation plane, measure a second distance which is a nearest neighbor distance between any position on a surface of a second region specified in the medical image and the separation plane, and display at least one of first distance information indicating the first distance or second distance information indicating the second distance in a case where the medical image is displayed on a display device.

13 Claims, 22 Drawing Sheets

(51) Int. Cl.

| | |
|---|---|
| ***G06T 7/00*** | (2017.01) |
| ***G06T 7/73*** | (2017.01) |
| ***G06T 15/08*** | (2011.01) |
| ***G06T 15/20*** | (2011.01) |
| ***G16H 30/40*** | (2018.01) |

(52) U.S. Cl.

CPC ............. *G06T 15/20* (2013.01); *G16H 30/40* (2018.01); *A61B 6/50* (2013.01); *G06T 2200/04* (2013.01); *G06T 2207/10024* (2013.01); *G06T 2207/10088* (2013.01); *G06T 2207/20021* (2013.01); *G06T 2207/30028* (2013.01); *G06T 2207/30096* (2013.01); *G06T 2210/41* (2013.01)

(58) Field of Classification Search

CPC . G06T 2207/10024; G06T 2207/10088; G06T 2207/20021; G06T 2207/30028; G06T 2207/30096; G06T 2210/41; G16H 30/40; A61B 6/50

See application file for complete search history.

(56) References Cited

U.S. PATENT DOCUMENTS

| | | | | |
|---|---|---|---|---|
| 2018/0055575 | A1 | 3/2018 | Krimsky | |
| 2020/0242776 | A1 | 7/2020 | Nagata et al. | |
| 2021/0121235 | A1* | 4/2021 | Wei | A61B 17/07207 |
| 2021/0264644 | A1* | 8/2021 | Zhang | G06T 7/0012 |
| 2021/0398304 | A1 | 12/2021 | Uyama et al. | |
| 2022/0005258 | A1* | 1/2022 | Mory | A61B 8/5261 |
| 2022/0118713 | A1* | 4/2022 | Vignat | B29C 64/40 |
| 2023/0070102 | A1* | 3/2023 | Mory | G06T 15/503 |

FOREIGN PATENT DOCUMENTS

| | | |
|---|---|---|
| JP | 2011218037 | 11/2011 |
| JP | 2012165910 | 9/2012 |
| JP | 2016039874 | 3/2016 |
| JP | 2020074926 | 5/2020 |
| JP | 2020120828 | 8/2020 |
| WO | 2017047820 | 3/2017 |

OTHER PUBLICATIONS

Petroudi, S., Brown, G., Bond, S., & Brady, M. (Aug. 2006). Circumferential resection margin assessment on MRI of rectal cancer. In 2006 International Conference of the IEEE Engineering in Medicine and Biology Society (pp. 4881-4884) (Year: 2006).*

C. A. Morariu, M. Thomas, J. Pauli, D. S. Dohle and K. Tsagakis, "Sequential vs. batch machine-learning with evolutionary hyperparameter optimization for segmenting aortic dissection thrombus," 2016 23rd International Conference on Pattern Recognition (ICPR), Cancun, Mexico, 2016 (Year: 2016).*

Palomar, R., Cheikh, F. A., Edwin, B., Fretland, Å., Beghdadi, A., & Elle, O. J. (2017). A novel method for planning liver resections using deformable Bézier surfaces and distance maps. Computer methods and programs in biomedicine, 144, 135-145 (Year: 2017).*

N. Smit et al., "PelVis: Atlas-based Surgical Planning for Oncological Pelvic Surgery," in IEEE Transactions on Visualization and Computer Graphics, vol. 23, No. 1, pp. 741-750, Jan. 2017, doi: 10.1109/TVCG.2016.2598826 (Year: 2017).*

Lubbers, H. T., Obwegeser, J. A., Matthews, F., Eyrich, G., Grätz, K. W., & Kruse, A. (2011). A simple and flexible concept for computer-navigated surgery of the mandible. Journal of oral and maxillofacial surgery, 69(3), 924-930 (Year: 2011).*

"Search Report of Europe Counterpart Application No. 22756192.5", issued on Jun. 20, 2024, p. 1-p. 8.

David F. Marshall et al., "Interactive visualisation for surface proximity monitoring", Proceedings of the 16th Australasian User Interface Conference (AUIC 2015), vol. 162, Jan. 2015, pp. 41-50.

Styliani Petroudi et al., "Circumferential resection margin assessment on MRI of rectal cancer", Conference Proceedings. Annual International Conference of the IEEE Engineering in Medicine and Biology Society, Sep. 2006, pp. 4881-4884.

Heinz-Theo Lubbers et al., "A simple and flexible concept for computer-navigated surgery of the mandible", J Oral Maxillofac Surg, Jun. 2010, pp. 924-930.

"Office Action of Europe Counterpart Application", issued on May 30, 2025, p. 1-p. 6.

"International Search Report (Form PCT/ISA/210) of PCT/JP2022/006046," mailed on Apr. 12, 2022, with English translation thereof, pp. 1-5.

"Written Opinion of the International Searching Authority (Form PCT/ISA/237) of PCT/ JP2022/006046," mailed on Apr. 12, 2022, with English translation thereof, pp. 1-6.

Christian Hansen et al., "Risk Maps for Liver Surgery", International Journal of Computer Assisted Radiology and Surgery, Sep. 2012, pp. 1-12.

"Office Action of Europe Counterpart Application", issued on Apr. 2, 2026, pp. 1-6.

* cited by examiner 20
222
IMAGE ACQUISITION UNIT
224
LESION REGION EXTRACTION UNIT
226
LESION REGION INPUT RECEPTION UNIT
228
RESECTION PLANE EXTRACTION UNIT
230
RESECTION PLANE INPUT RECEPTION UNIT
232
DISTANCE MEASUREMENT UNIT
234
DISPLAY IMAGE GENERATION UNIT
214
INPUT DEVICE
216
DISPLAY DEVICE

Figure 11:
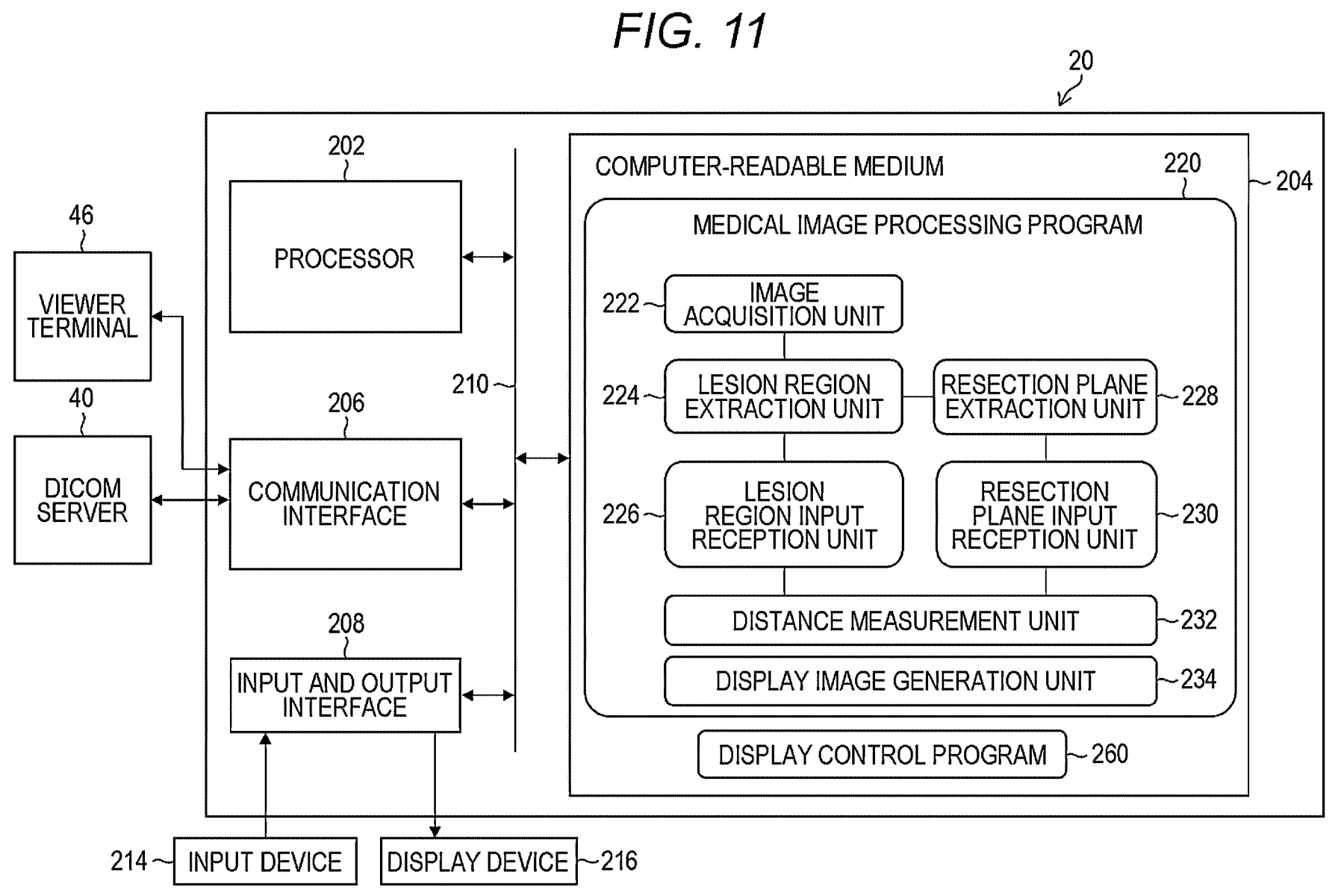

COMPUTER-READABLE MEDIUM

220

MEDICAL IMAGE PROCESSING PROGRAM

222 IMAGE ACQUISITION UNIT

224 LESION REGION EXTRACTION UNIT

226 LESION REGION INPUT RECEPTION UNIT

228 RESECTION PLANE EXTRACTION UNIT

230 RESECTION PLANE INPUT RECEPTION UNIT

232 DISTANCE MEASUREMENT UNIT

234 DISPLAY IMAGE GENERATION UNIT

260 DISPLAY CONTROL PROGRAM

210

202 PROCESSOR

206 COMMUNICATION INTERFACE

208 INPUT AND OUTPUT INTERFACE

216 DISPLAY DEVICE

214 INPUT DEVICE

46 VIEWER TERMINAL

40 DICOM SERVER

FIG. 13
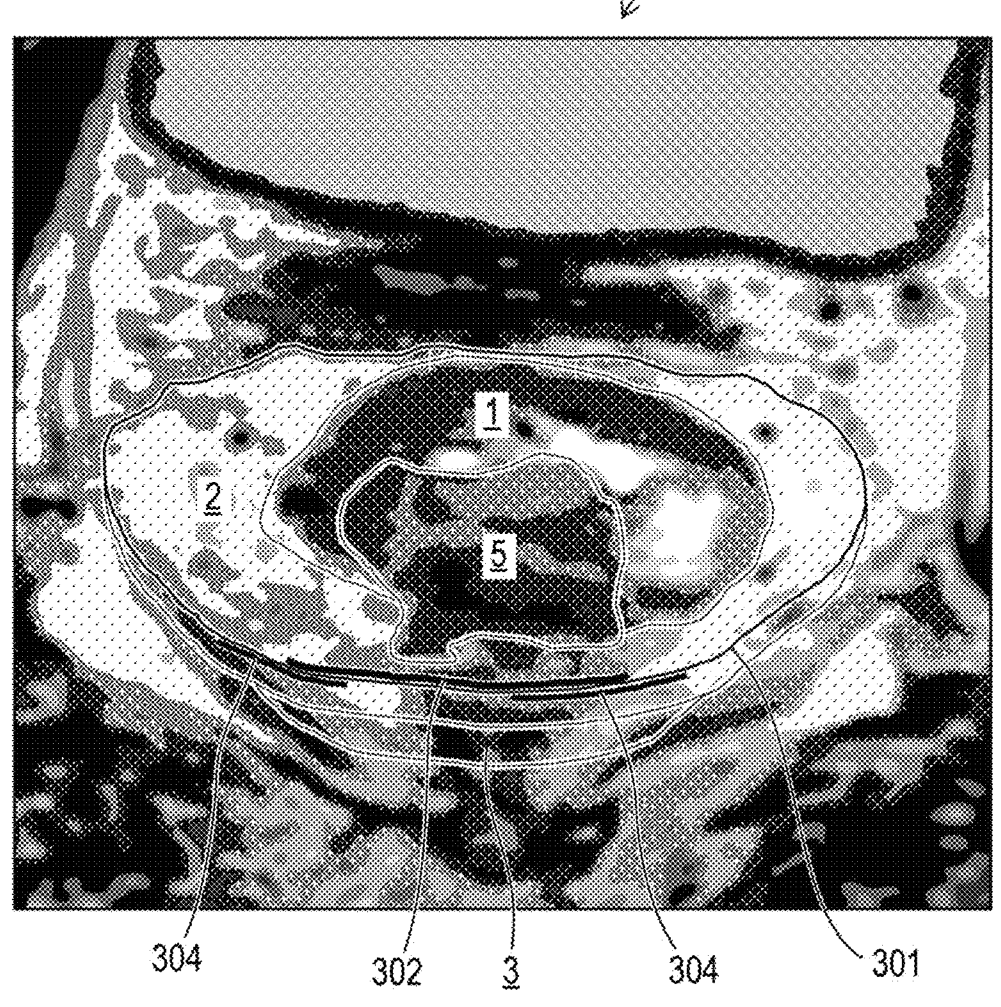

FIG. 14
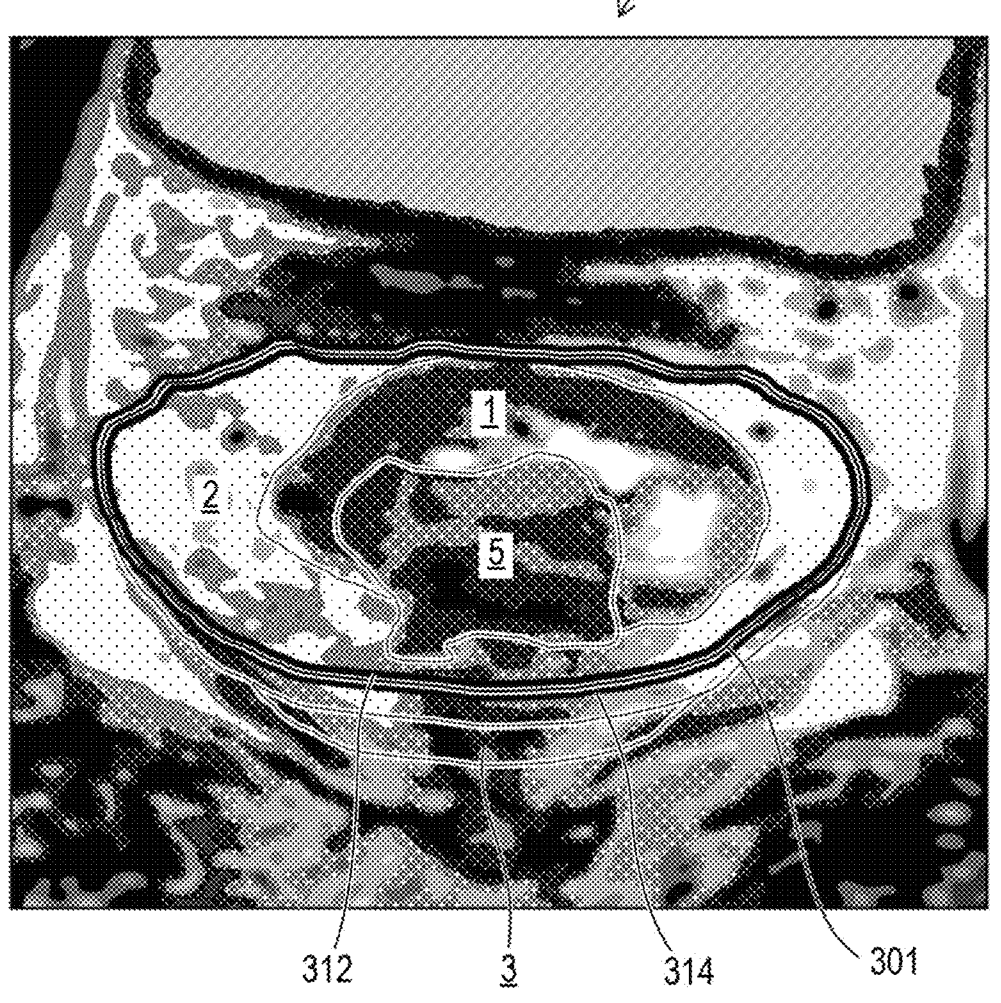

100
40
DICOM SERVER
20
MEDICAL IMAGE PROCESSING APPARATUS
44
ELECTRONIC MEDICAL RECORD SYSTEM
48
30
31
CT APPARATUS
32
MRI APPARATUS
33
ULTRASOUND DIAGNOSTIC APPARATUS
34
PET APPARATUS
35
X-RAY DIAGNOSTIC APPARATUS
36
X-RAY FLUOROSCOPIC DIAGNOSTIC APPARATUS
37
ENDOSCOPE APPARATUS
46
VIEWER TERMINAL
46
VIEWER TERMINAL
46
VIEWER TERMINAL

MEDICAL IMAGE PROCESSING APPARATUS, MEDICAL IMAGE PROCESSING METHOD, AND PROGRAM

CROSS-REFERENCE TO RELATED APPLICATIONS

The present application is a Continuation of PCT International Application No. PCT/JP2022/006046 filed on Feb. 16, 2022 claiming priority under 35 U.S.C § 119(a) to Japanese Patent Application No. 2021-026334 filed on Feb. 22, 2021. Each of the above applications is hereby expressly incorporated by reference, in its entirety, into the present application.

BACKGROUND OF THE INVENTION

1. Field of the Invention

The present invention relates to a medical image processing apparatus, a medical image processing method, and a program.

2. Description of the Related Art

Rectal cancer arises from a lumen of an intestinal tract and infiltrates tissue outside the intestinal tract as the cancer progresses. For highly advanced cancer that requires a surgical operation, total mesorectal excision is performed to excise the entire mesorectum, which is fat tissue surrounding the periphery of the rectum. TME is an abbreviation for the English expression total mesorectal excision.

In surgery in which total mesorectal excision is performed, it is required to achieve both resection with a sufficient margin around the cancer and preservation of important tissue around the mesorectum, such as nerves and blood vessels.

As a background in which resection with a sufficient margin is required, a case is exemplified where a circumferential resection margin (CRM), which is a distance between the cancer and a dissection plane around the rectum, is 1 millimeter or less is considered a strong predictor of local recurrence.

On the other hand, as a background in which the preservation of tissue around the mesorectum is required, a case is exemplified where thin blood vessels, autonomic nerves, and the like around the mesorectum are present. In a case where autonomic nerves or the like are damaged, dysuria, sexual dysfunction, and the like may be caused by the damage of the autonomic nerves or the like.

Yusuke Kinugasa, "A dissection layer for the operation of the perirectal fascia and function-preserving rectal cancer as viewed from surgeons" [online], Sep. 8, 2012, Japanese Research Society of Clinical Anatomy, retrieved on Jan. 25, 2021, the Internet (http://www.jrsca.jp/contents/records/contents/PDF/13-PDF/p08.pdf), describes that, in function-sparing surgery for rectal cancer, a dissection layer is selected in accordance with the progress of the cancer to ensure a radical cure. This literature also describes that nerve damage increases or decreases depending on the level of the dissection layer.

JP2016-039874A discloses an endoscopic image diagnosis support apparatus that displays a distance distribution from a bronchial wall to a region of interest outside a bronchus such that the distance distribution is superimposed on a volume rendering image. The apparatus disclosed in JP2016-039874A generates a first projection image and a second projection image obtained by projecting a region of interest on an inner wall of a bronchus using a three-dimensional image. The first projection image and the second projection image are highlighted according to the projection distance.

WO2017/047820A discloses a blood flow visualization apparatus that automatically analyzes a blood vessel lesion using a computer. The apparatus disclosed in WO2017/047820A acquires a medical image, determines a vascular lesion using a blood vessel shape constructed from the medical image, and calculates a geometric feature of the vascular lesion.

JP2011-218037A describes a medical image processing apparatus that measures the thickness of a fat region present around a coronary artery. The apparatus described in JP2011-218037A measures the distribution and thickness of a fat region formed around a coronary artery based on volume data, and generates two-dimensional fat thickness distribution data.

JP2009-022369A discloses a technique for displaying an image used for a surgical plan for breast cancer resection surgery. The image processing apparatus described in JP2009-022369A generates a VR image or the like using reconstructed data, specifies a tumor range, calculates a distance from a reference point to the tumor range on a body surface, and displays the distance on the VR image.

JP2020-120828A discloses a medical image processing apparatus that divides an organ of a subject into a plurality of areas, corrects end portions of the areas and a boundary between the areas, and calculates a resection target region in the organ using a result of the division.

SUMMARY OF THE INVENTION

However, in order to consider, before surgery, a dissection plane capable of achieving both the resection of a lesion with a sufficient margin around the lesion such as cancer and the preservation of important tissue around the lesion, it is necessary to know a three-dimensional distance between tissue to be resected and tissue to be preserved and a three-dimensional distance between the dissection plane and the tissue to be resected.

In order to know the three-dimensional distance between the tissue to be resected and the tissue to be preserved, it is necessary to determine whether or not the tissue targeted for the measurement of the three-dimensional distance, a dissection plane to be set, and the like are selected at correct positions in a medical image. Such determination requires evaluation in a two-dimensional cross-sectional image of the three-dimensional medical image. That is, to consider the dissection plane, it is required to display a spatial distance between targets for the measurement of the three-dimensional distance in the two-dimensional cross-sectional image in an easily understandable manner.

In JP2016-039874A, WO2017/047820A, JP2011-218037A, JP2009-022369A, and JP2020-120828A, there is no description regarding display at the time of evaluating a three-dimensional distance between a dissection plane for dissecting tissue to be resected and the tissue to be resected and a three-dimensional distance between the dissection plane and tissue to be preserved, and means for solving such a problem is not described.

The present invention has been made in view of such circumstances, and it is an object of the present invention to provide a medical image processing apparatus, a medical image processing method, and a program capable of supporting determination of a separation plane based on a three-dimensional distance between tissue to be resected and tissue to be preserved.

According to a first aspect, there is provided a medical image processing apparatus including a processor and a storage device in which a program executed using the processor is stored, in which the processor executes a command of the program to acquire a three-dimensional medical image, set a separation plane for separating a first region specified in the medical image, measure a first distance which is a nearest neighbor distance between any position on a surface of the first region and the separation plane, measure a second distance which is a nearest neighbor distance between any position on a surface of a second region specified in the medical image and the separation plane, and display at least one of first distance information indicating the first distance or second distance information indicating the second distance in a case where the medical image is displayed on a display device.

According to the first aspect, in the medical image processing apparatus, at least one of the three-dimensional distance between the first region and the separation plane or the three-dimensional distance between the second region and the separation plane can be ascertained at a glance, and the determination of the separation plane can be supported.

In the first region, a region including tissue to be separated can be specified. In the second region, a region including tissue to be preserved can be specified.

A third region present between the first region and the second region can be used as a region where the separation plane is designated.

According to a second aspect, in the medical image processing apparatus, the processor displays the first distance information in an outer edge region of the separation plane on a first region side in a case where a cross-sectional image corresponding to any cross section in the medical image is displayed on the display device.

According to the second aspect, the obstruction of the visibility of the separation plane can be suppressed. In addition, the side on which the first distance is applied with respect to the separation plane can be ascertained at a glance.

The edge region may be a region that is in contact with the separation plane or may be a region that is not in contact with the separation plane.

According to a third aspect, in the medical image processing apparatus, the processor displays the second distance information in an outer edge region of the separation plane on a second region side in a case where a cross-sectional image corresponding to any cross section in the medical image is displayed on the display device.

According to the third aspect, the obstruction of the visibility of the separation plane can be suppressed. In addition, the side on which the second distance is applied with respect to the separation plane can be ascertained at a glance.

According to a fourth aspect, in the medical image processing apparatus, the processor displays the first distance information and the second distance information by applying a color map representing a distance using a color.

According to the fourth aspect, the first distance and the second distance can be ascertained at a glance based on information represented by the color of the color map.

Examples of the color map include a form in which a difference in color represents a difference in distance and a form in which a difference in density represents a difference in distance.

According to a fifth aspect, in the medical image processing apparatus, the processor displays a volume rendering image corresponding to the medical image on the display device and displays at least one of the first distance information or the second distance information superimposed on the volume rendering image.

According to the fifth aspect, in the volume rendering image, at least one of the three-dimensional distance between the first region and the separation plane or the three-dimensional distance between the second region and the separation plane can be ascertained at a glance, and the determination of the separation plane can be supported.

According to a sixth aspect, in the medical image processing apparatus, the processor changes a display form of the first distance information and a display form of the second distance information according to a user's viewpoint in the volume rendering image.

According to the sixth aspect, the first distance and the second distance as viewed from the user's viewpoint can be ascertained at a glance.

According to a seventh aspect, in the medical image processing apparatus, the processor displays the first distance information superimposed on the first region in a case where the first region is present on the user's viewpoint side of the separation plane in the volume rendering image.

According to the seventh aspect, the first distance information can be displayed at a position viewable from the user's viewpoint in the first region viewable from the user's viewpoint.

According to an eighth aspect, in the medical image processing apparatus, the processor displays the second distance information superimposed on the separation plane in a case where the second region is present on an opposite side of the user's viewpoint with respect to the separation plane in the volume rendering image.

According to the eighth aspect, the second distance information can be displayed at a position viewable from the user's viewpoint in the second region not viewable from the user's viewpoint.

According to a ninth aspect, in the medical image processing apparatus, the processor displays the first distance information superimposed on the separation plane in a case where the first region is present on an opposite side of the user's viewpoint with respect to the separation plane in the volume rendering image.

According to the ninth aspect, the first distance information can be displayed at a position viewable from the user's viewpoint in the first region not viewable from the user's viewpoint.

According to a tenth aspect, in the medical image processing apparatus, the processor displays the second distance information superimposed on the second region in a case where the second region is present on the user's viewpoint side of the separation plane in the volume rendering image.

According to the tenth aspect, the second distance information can be displayed at a position viewable from the user's viewpoint in the second region viewable from the user's viewpoint.

According to an eleventh aspect, there is provided a medical image processing method including, via a computer: acquiring a three-dimensional medical image; setting a separation plane for separating a first region specified in the medical image; measuring a first distance which is a nearest neighbor distance between any position on a surface of the first region and the separation plane; measuring a second distance which is a nearest neighbor distance between any position on a surface of a second region specified in the medical image and the separation plane; and displaying at least one of first distance information indicating the first distance or second distance information indicating the second distance in a case where the medical image is displayed on a display device.

According to the eleventh aspect, in the medical image processing method, it is possible to obtain the same effects as those of the medical image processing apparatus according to the present disclosure. The constituent elements of the medical image processing apparatus according to the other aspects can be applied to constituent elements of the medical image processing method according to other aspects.

According to a twelfth aspect, there is provided a program causing a computer to implement: a function of acquiring a three-dimensional medical image; a function of setting a separation plane for separating a first region specified in the medical image; a function of measuring a first distance which is a nearest neighbor distance between any position on a surface of the first region and the separation plane; a function of measuring a second distance which is a nearest neighbor distance between any position on a surface of a second region specified in the medical image and the separation plane; and a function of displaying at least one of first distance information indicating the first distance or second distance information indicating the second distance in a case where the medical image is displayed on a display device.

According to the twelfth aspect, in the program, it is possible to obtain the same effects as those of the medical image processing apparatus according to the present disclosure. The constituent elements of the medical image processing apparatus according to the other aspects may be applied to constituent elements of the program according to other aspects.

According to a thirteenth aspect, at least one of the three-dimensional distance between the first region and the separation plane or the three-dimensional distance between the second region and the separation plane can be ascertained at a glance, and the determination of the separation plane can be supported.

BRIEF DESCRIPTION OF THE DRAWINGS

FIG. 11 is a block diagram illustrating an example of a configuration of the medical image processing apparatus according to the embodiment.

FIG. 13 is an image diagram illustrating an example in which three-dimensional distance information is superimposed and displayed on a two-dimensional cross section.

FIG. 14 is an image diagram illustrating another example in which three-dimensional distance information is superimposed and displayed on a two-dimensional cross section.

DESCRIPTION OF THE PREFERRED EMBODIMENTS

Figure 1:
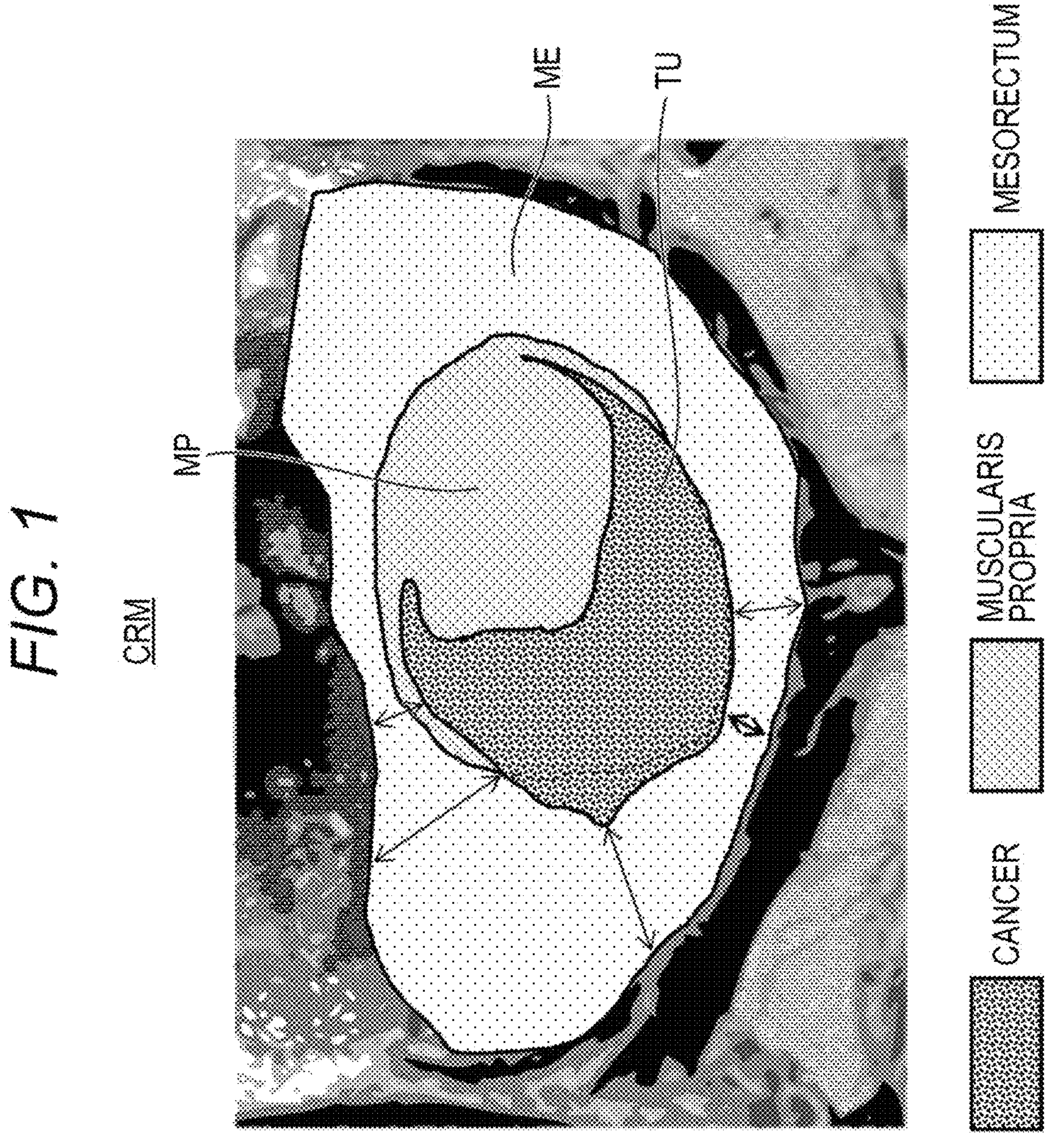
FIG. 1 is a diagram illustrating an example in which a CRM is measured from an MM image obtained by imaging a patient with rectal cancer.

Hereinafter, preferred embodiments of the present invention will be described in detail with reference to the accompanying drawings. In this specification, the same components are denoted by the same reference numerals, and redundant description will be omitted as appropriate.

Example of Distance Measurement for Rectal Cancer

FIG. 1 is a diagram illustrating an example in which a CRM is measured from an MM image obtained by imaging a patient with rectal cancer. In FIG. 1, a cancer TU, a muscularis propria MP, and a mesorectum ME are distinguished from each other by different shading patterns. Although FIG. 1 illustrates a two-dimensional image, the actually acquired MRI image is a three-dimensional image. MM is an abbreviation for magnetic resonance imaging.

Modalities such as an MRI apparatus and a CT apparatus continuously capture two-dimensional slice images to obtain three-dimensional data indicating a three-dimensional form of a target object. The term "three-dimensional image" may include a concept of a collection and two-dimensional sequence of two-dimensional slice images continuously captured. The term "image" can include a meaning of image data. CT is an abbreviation for computed tomography.

An arrow line illustrated in FIG. 1 represents a closest portion where the distance from the cancer TU to the mesorectum ME is shortest. In a case where the degree of progress of the cancer is determined, a nearest neighbor distance which is the distance of the closest portion is one of the important parameters. In a case where the nearest neighbor distance is equal to or less than 1 millimeter, it is determined as CRM positive.

<Description of Low Anterior Resection>

Figure 2:
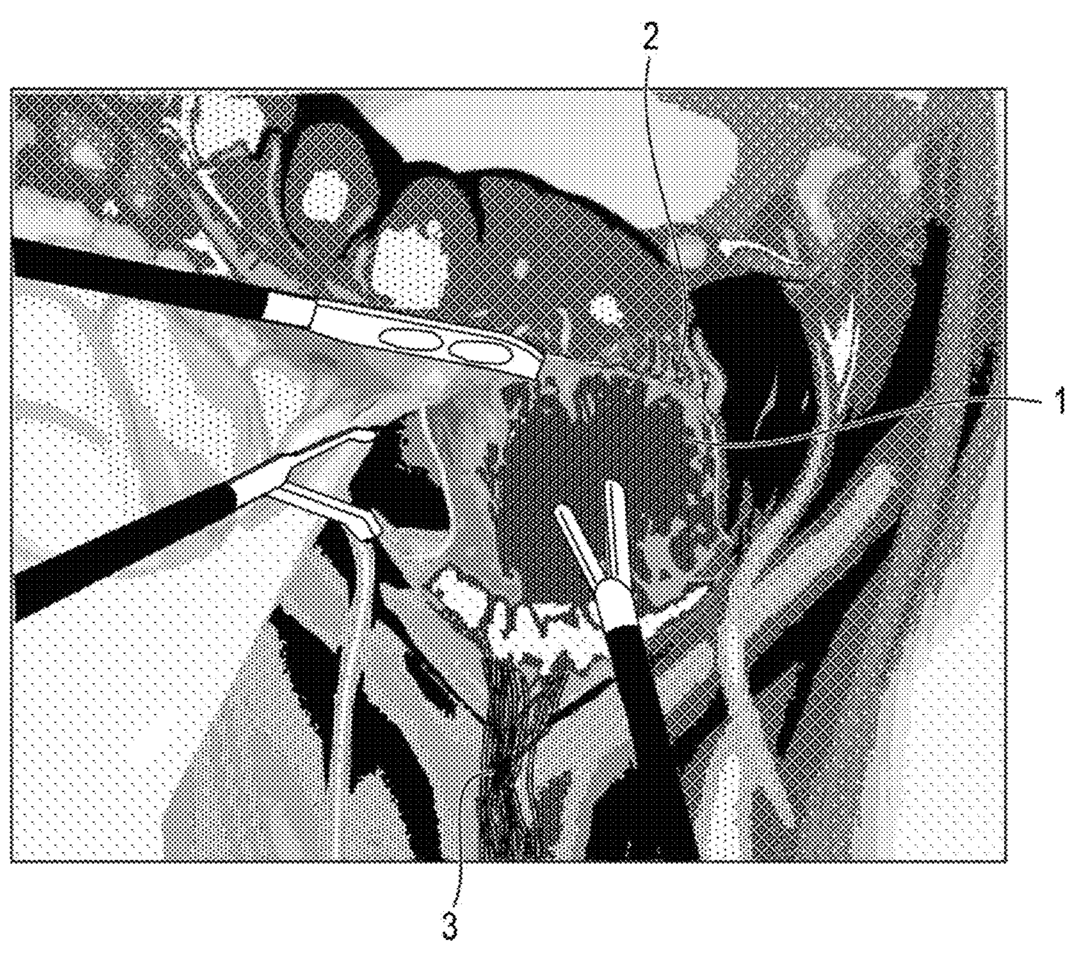
FIG. 2 is a diagram illustrating a low anterior resection.
Figure 3:
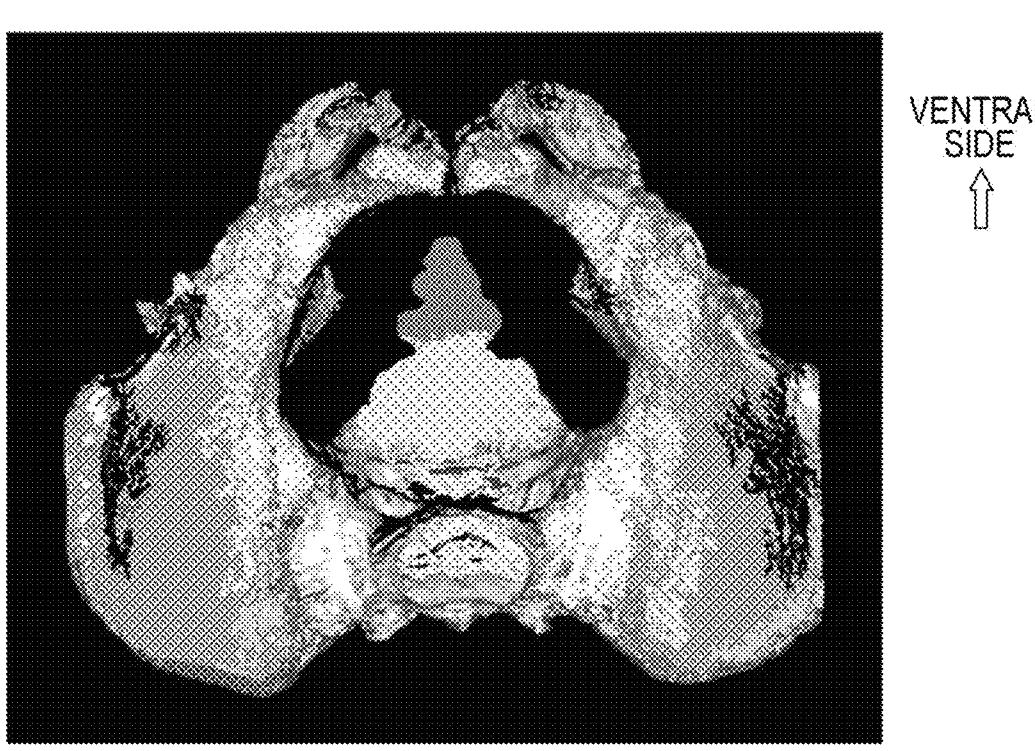
FIG. 3 is an image diagram illustrating the orientation of FIG. 2.

FIG. 2 is a diagram illustrating a low anterior resection. FIG. 3 is an image diagram illustrating the orientation of FIG. 2. FIG. 2 is a view of the inside of a pelvis as viewed from a head side. FIG. 3 illustrates a position on a ventral side in FIG. 2 using an arrow line.

FIG. 2 illustrates a state where the cancer is resected by performing the low anterior resection in which fat 2 around a rectum 1 in which the cancer occurred is dissected and the whole cancer is resected. In a case where the cancer is resected, it is important to completely resect the cancer without damaging a nerve 3.

Figure 4:
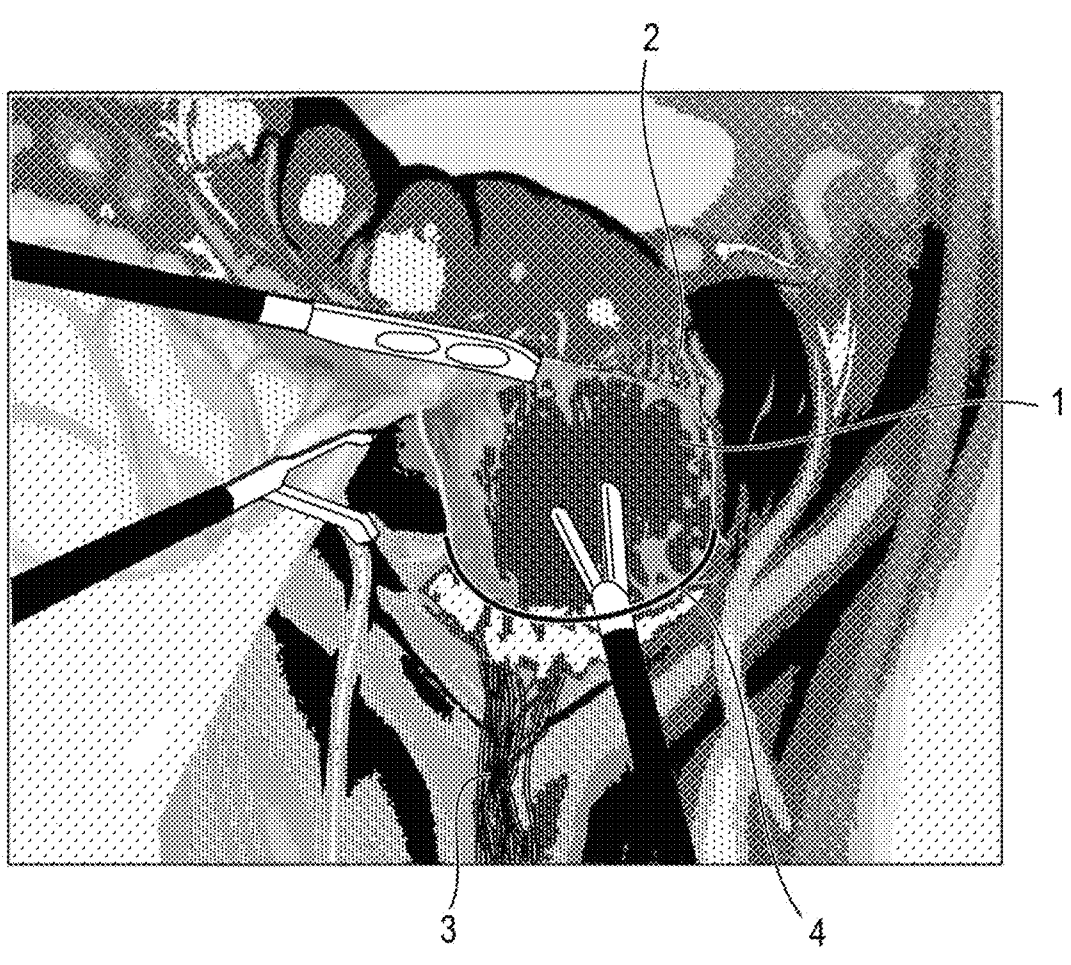
FIG. 4 is a diagram illustrating a resection plane.

FIG. 4 is a diagram illustrating a resection plane. In a case where the cancer is resected, the cancer is resected on the resection plane 4. In a case where the resection plane 4 is too close to the inside of the rectum 1, the cancer is exposed. On the other hand, in a case where the resection plane 4 is excessively outside the rectum 1, the nerve 3 may be damaged.

Figure 5:
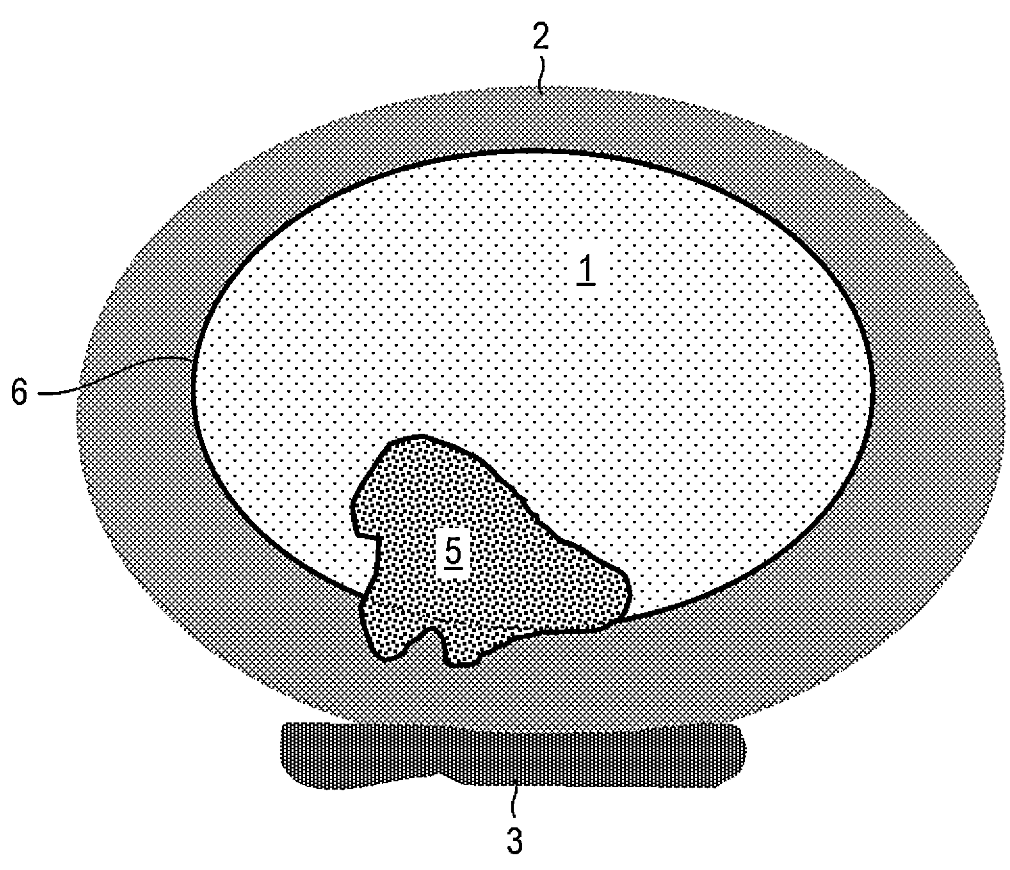
FIG. 5 is a schematic diagram illustrating an arbitrary cross section of the MRI image.
Figure 6:
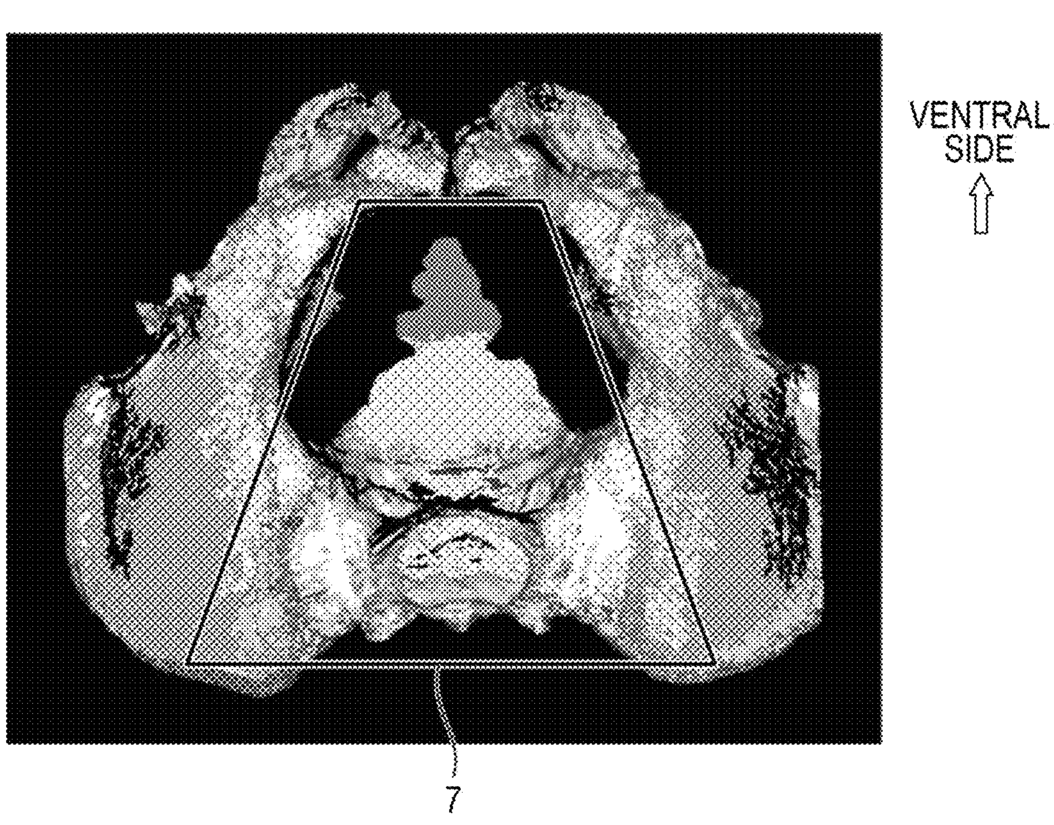
FIG. 6 is an image diagram illustrating the orientation of FIG. 5.

FIG. 5 is a schematic diagram illustrating an arbitrary cross section of the MRI image. FIG. 5 illustrates a state where a cancer 5 that has occurred in the rectum 1 reaches the fat 2 beyond a boundary 6 between the rectum 1 and the fat 2. FIG. 6 is an image diagram illustrating the orientation of FIG. 5. A region 7 illustrated in FIG. 6 represents a region where the rectum 1 and the like illustrated in FIG. 5 are present. The rectum 1, the fat 2, and the cancer 5 illustrated in FIG. 5 respectively correspond to the muscularis propria MP, the mesorectum ME, and the cancer TU illustrated in FIG. 1.

Figure 7:
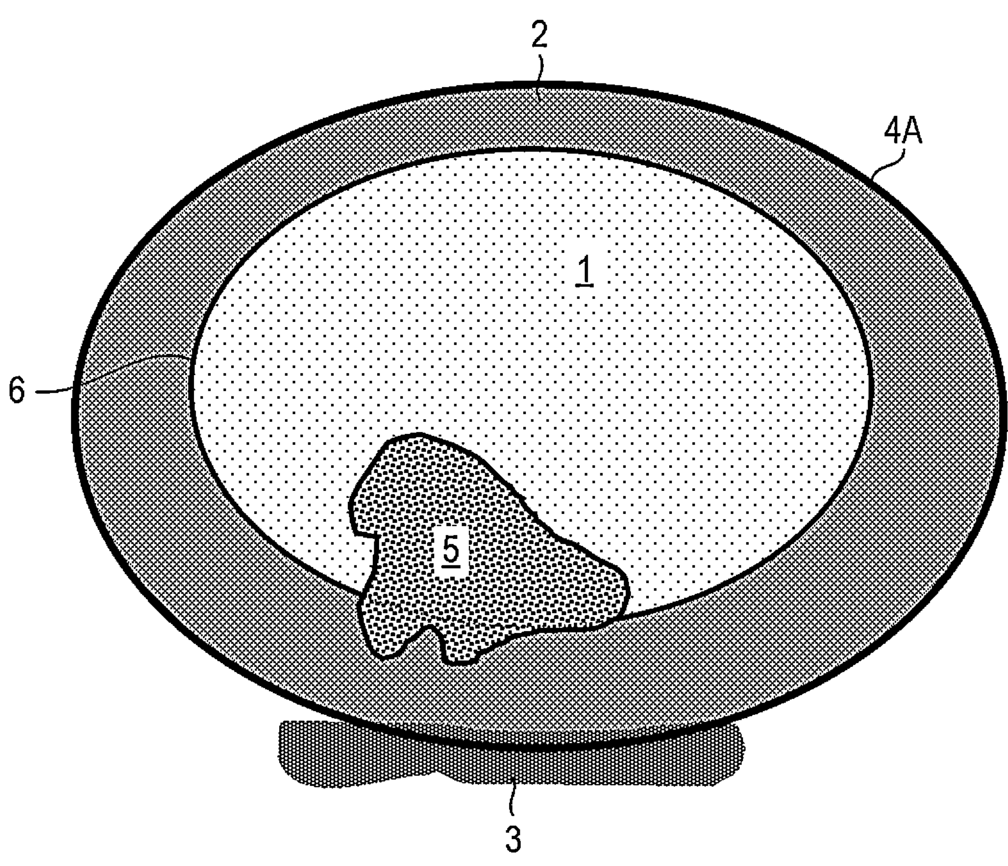
FIG. 7 is a schematic diagram illustrating a first example of a resection line.

FIG. 7 is a schematic diagram illustrating a first example of a resection line. The resection line 4A illustrated in FIG. 7 is set in a case where the cancer 5 is resected together with the fat 2 around the rectum 1 in which the cancer 5 has occurred. That is, the resection line 4A matches the contour of the fat 2.

In a case where the resection line 4A is set, the nerve 3 may be damaged when the cancer 5 is resected. The resection line 4A in a cross-sectional image illustrated in FIG. 7 corresponds to the resection plane 4 illustrated in FIG. 4. The same applies to a resection line 4B illustrated in FIG. 8 and a resection line 4C illustrated in FIG. 9.

Figure 8:
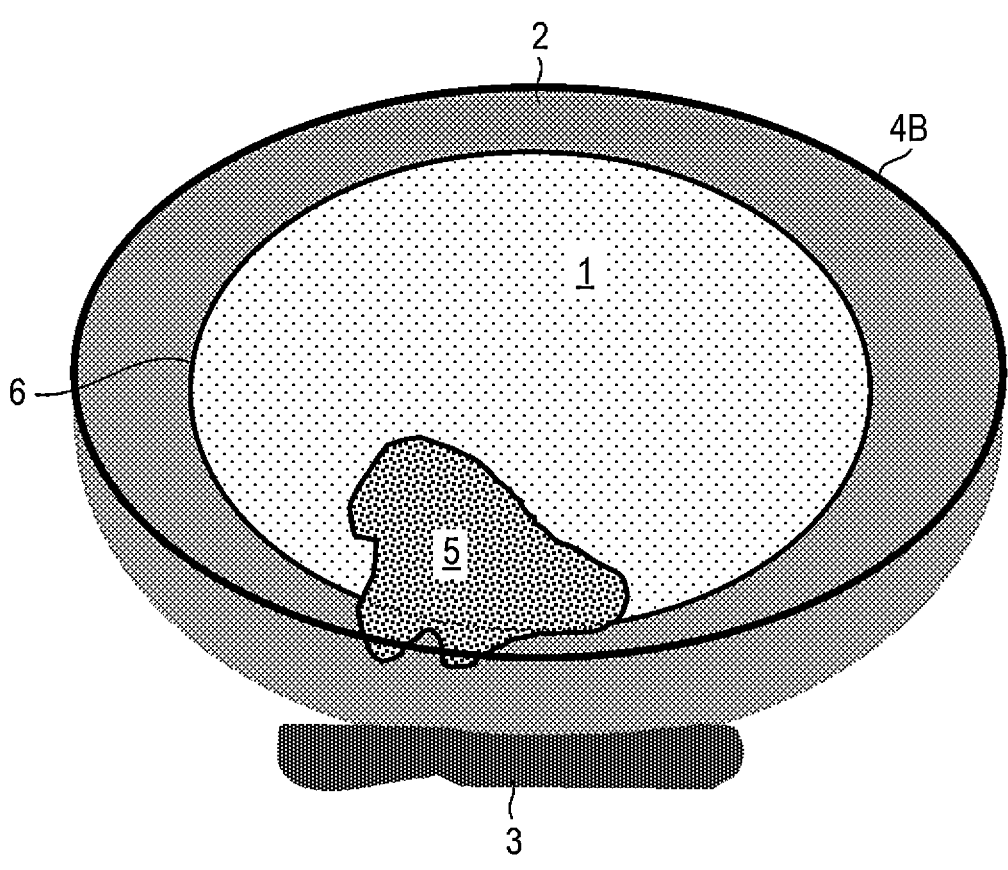
FIG. 8 is a schematic diagram illustrating a second example of the resection line.

FIG. 8 is a schematic diagram illustrating a second example of the resection line. The resection line 4B illustrated in FIG. 8 is set in a case where the cancer 5 is resected while avoiding the nerve 3 and leaving a part of the fat 2. That is, a part of the resection line 4B matches the contour of the fat 2, and a part of the resection line 4B is inside the fat 2. In a case where the resection line 4B is set, the cancer 5 may not be completely removed.

Figure 9:
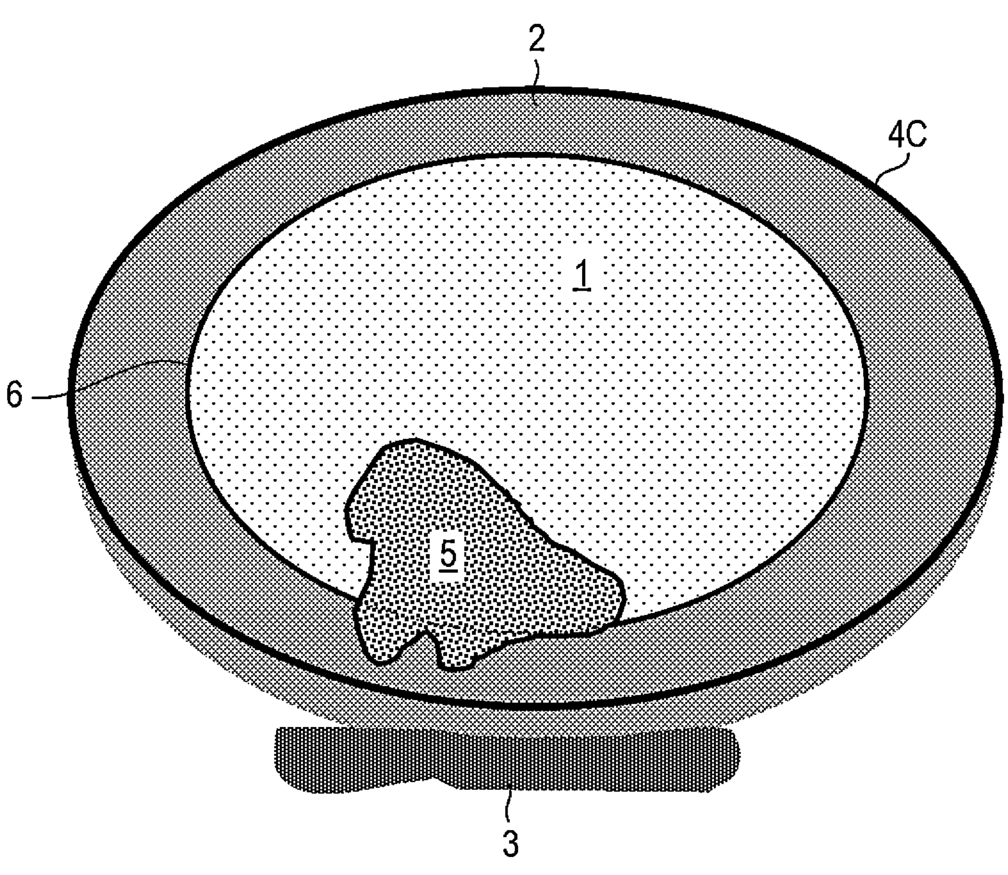
FIG. 9 is a schematic diagram illustrating a third example of the resection line.

FIG. 9 is a schematic diagram illustrating a third example of the resection line. The resection line 4C illustrated in FIG. 9 is set in a case where the cancer 5 is resected while avoiding the nerve 3 and leaving a part of the fat 2. That is, similarly to the resection line 4B illustrated in FIG. 8, a part of the resection line 4C matches the contour of the fat 2, and a part of the resection line 4C is inside the fat 2, while a sufficient margin from the nerve 3 and a sufficient margin from the cancer 5 are taken for the resection line 4C.

In a case where the resection plane 4 illustrated in FIG. 4 is set, a medical image processing apparatus described below measures three-dimensional distances between the cancer 5, which is the tissue to be resected, and tissue to be preserved, such as the nerve 3 and a blood vessel, displays the measurement results on a two-dimensional cross-sectional image, and supports the determination of the resection plane 4.

From a medical image such as the MRI image, the three-dimensional distance between tissue to be preserved and the resection plane 4 illustrated in FIG. 4 is ascertained, and the three-dimensional distance between the tissue to be resected such as the cancer 5 illustrated in FIG. 9 and the resection plane 4 is ascertained.

Accordingly, the resection plane 4 on which a sufficient margin from the tissue to be preserved is obtained and a sufficient margin from the tissue to be resected is obtained can be planned before surgery. In a case where it is found in advance that a sufficient margin cannot be obtained, the preservation of the tissue to be preserved may be given up, and a surgical technique for resecting the nerve 3, a blood vessel, and the like may be selected.

Example of Configuration of Medical Image Processing Apparatus

Figure 10:
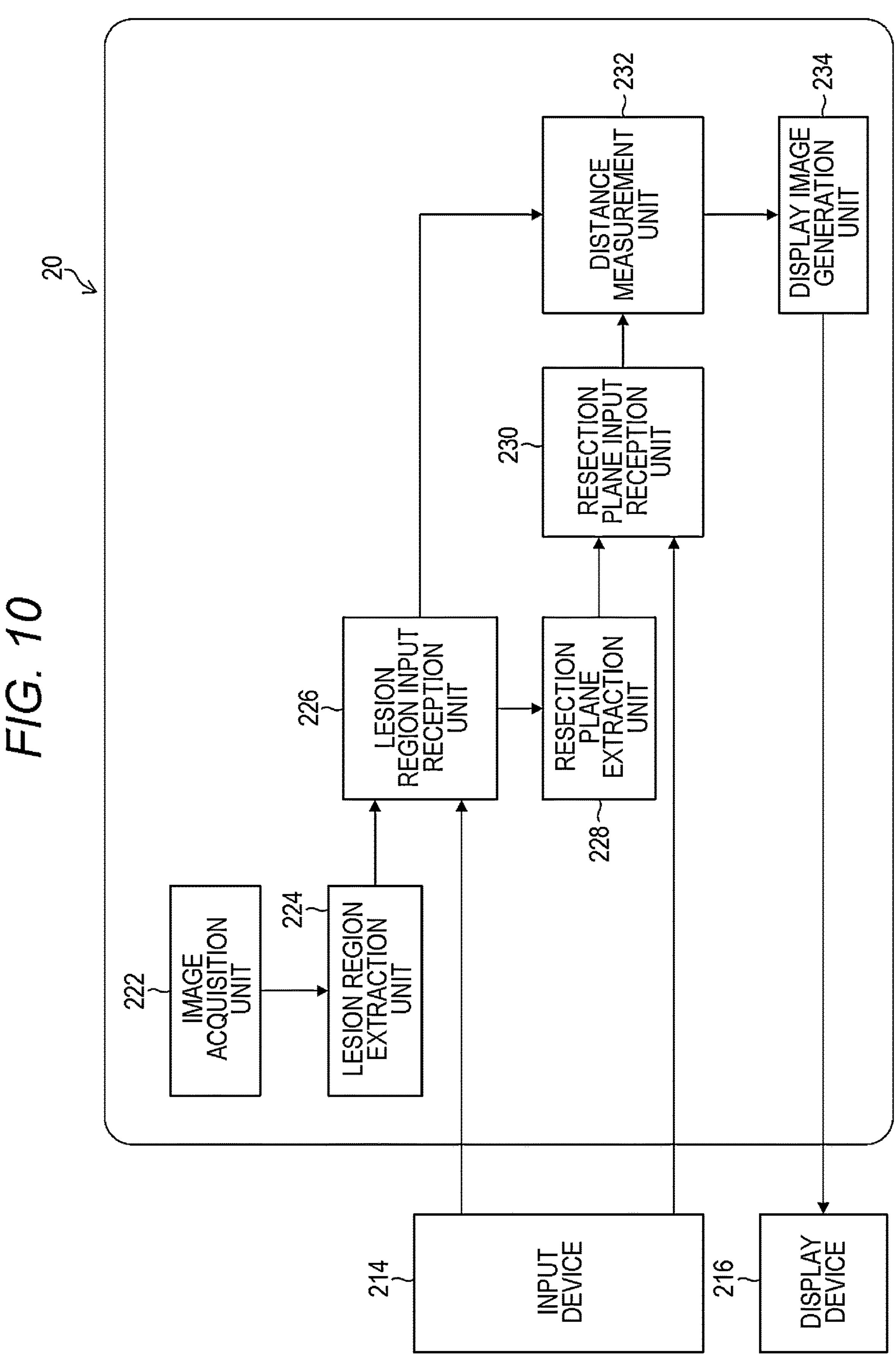
FIG. 10 is a functional block diagram of a medical image processing apparatus according to an embodiment.

FIG. 10 is a functional block diagram of a medical image processing apparatus according to an embodiment. A medical image processing apparatus 20 illustrated in FIG. 10 is implemented using hardware and software of a computer. The software is synonymous with a program. The term "medical image" used in the embodiments described below is synonymous with the term "medical image".

The medical image processing apparatus 20 includes an image acquisition unit 222, a lesion region extraction unit 224, a lesion region input reception unit 226, a resection plane extraction unit 228, a resection plane input reception unit 230, a distance measurement unit 232, and a display image generation unit 234. An input device 214 and a display device 216 are connected to the medical image processing apparatus 20.

The image acquisition unit 222 acquires a medical image to be processed from an image storage server or the like. In the present embodiment, an MRI image captured using an MRI apparatus is exemplified as the medical image to be processed. The medical image to be processed is not limited to the MRI image, and may be an image captured by another modality such as a CT apparatus.

In the present embodiment, image diagnosis of cancer occurring in a digestive tract such as a large intestine is assumed, and examples of the medical image acquired via the image acquisition unit 222 include a three-dimensional image obtained as a single image by imaging a region including the cancer and tissue around the cancer. In addition, since the medical image processing apparatus 20 measures a distance three-dimensionally in units of millimeters, it is preferable that a target image be high-resolution three-dimensional data of isotropic voxels.

The lesion region extraction unit 224 performs a lesion region extraction process of applying image recognition to automatically extract a lesion region included in the medical image from the medical image acquired via the image acquisition unit 222. The lesion region in the present embodiment is a region of the cancer. Examples of the process of the lesion region extraction unit 224 include a process of performing image segmentation on the input medical image using a trained model that has learned a task of image segmentation by applying machine learning represented by deep learning, and of extracting the lesion region.

Examples of the trained model for performing the image segmentation include a convolutional neural network. The convolutional neural network may be referred to as a CNN, which is an abbreviation for the English expression convolutional neural network.

The lesion region extraction unit 224 is not limited to a unit configured to perform the segmentation for classifying the lesion region and other regions, and may be configured to perform segmentation for classifying each of a plurality of regions around the lesion region. For example, the lesion region extraction unit 224 may receive an input of a three-dimensional image, classify regions such as a cancer region which is the lesion region and another peripheral organ which is a preservation region, and extract the lesion region and the preservation region using a model trained to output an image of a segmentation result with a mask pattern added thereto for each region.

The lesion region input reception unit 226 receives an input of information of the lesion region automatically extracted by using the lesion region extraction unit 224. In addition, the lesion region input reception unit 226 receives an input of information of the lesion region designated by a user using the input device 214. A doctor who is a user can use the input device 214 to freely designate a region different from the lesion region automatically extracted by the lesion region extraction unit 224. For example, the doctor can use the input device 214 to designate a region recognized as cancer or a region suspected of cancer among regions that have not been extracted as cancer in automatic extraction.

The lesion region described in the embodiment is an example of a first region specified in a medical image. The preservation region described in the embodiment is an example of a second region specified in the medical image.

The resection plane extraction unit 228 performs processing for extracting, from the medical image, a candidate for the resection plane 4 serving as a reference for the resection of the lesion region on the basis of the information of the lesion region obtained via the lesion region input reception unit 226. Since the extent of cancer spread varies depending on the stage of cancer progression, an appropriate candidate for the resection plane 4 is automatically extracted according to the stage of cancer progression. The candidate for the resection plane 4 may be a curved plane having any shape.

The resection plane input reception unit 230 receives an input of information of the candidate for the resection plane 4 automatically extracted by using the resection plane extraction unit 228. Further, the resection plane input reception unit 230 receives an input of information of a resection plane designated by the user using the input device 214. The doctor as the user can use the input device 214 to designate a resection plane 4 different from the candidate for the resection plane 4 automatically extracted by using the resection plane extraction unit 228.

The resection plane 4 different from the automatically extracted candidate for the resection plane 4 may be a plane obtained by correcting a part of the automatically extracted candidate for the resection plane 4. The resection plane 4 is determined based on the information input via the resection plane input reception unit 230. Similarly to the candidate for the resection plane 4, the resection plane 4 may be a curved plane having any shape.

For example, in a case of considering the resection plane before surgery, the doctor can designate not only an anatomically existing boundary surface or the like but also a virtual surface in a layer as a candidate for the resection plane 4. The resection plane 4 described in the embodiment is an example of a separation plane for separating the first region specified in the medical image.

The distance measurement unit 232 measures a three-dimensional distance from the cancer 5 to the resection plane 4 and a three-dimensional distance from the tissue to be preserved to the resection plane. The tissue to be preserved is located on the opposite side of the resection plane 4 from the cancer 5. Examples of the tissue to be preserved include the nerve 3 illustrated in FIG. 9.

In a case where the input of the designation of the lesion region is received from the user, a mode in which the distance from the designated region to the resection plane 4 is measured is possible. It is also possible to adopt a mode in which all lesion regions including the automatically extracted lesion region and the lesion region designated by the user are grouped and regarded as one lesion region as a whole, and the distance between the lesion region and the resection plane 4 is measured. Preferably, these measurement modes can be selected.

The following method may be applied as a distance measurement method. The distances between a plurality of points on the contour of the lesion region to be measured and points on the resection plane 4 that are the closest to the plurality of points are calculated, and the shortest distance between two points among the plurality of calculated distances is acquired as the nearest neighbor distance between the resection plane 4 and the lesion region.

Similarly to the measurement of the distance between the resection plane 4 and the lesion region, distances between the resection plane 4 and the preservation region are measured, and the nearest neighbor distance between the resection plane 4 and the preservation region is acquired. Each of the plurality of points on the contour of the lesion region described in the embodiment is an example of any position on a surface of the first region. Each of a plurality of points on the contour of the preservation region described in the embodiment is an example of any position on a surface of the second region.

The display image generation unit 234 generates a display image to be displayed on the display device 216. The display image generation unit 234 generates a two-dimensional image for display from a three-dimensional image. Examples of the two-dimensional image for display include a cross-sectional image and a volume rendering image.

The display image generation unit 234 generates at least one cross-sectional image among an axial cross-sectional image, a coronal cross-sectional image, and a sagittal cross-sectional image. The display image generation unit 234 may generate all of the three types of cross-sectional images described above.

The display image generation unit 234 generates an image representing the resection plane 4 determined using the resection plane extraction unit 228. The image representing the resection plane 4 is superimposed and displayed on the cross-sectional image or the like. Examples of the image representing the resection plane 4 superimposed and displayed on the cross-sectional image include the resection line 4C illustrated in FIG. 9.

The display image generation unit 234 generates first distance information indicating the distance between the resection plane 4 and the lesion region measured by the distance measurement unit 232. Further, the display image generation unit 234 generates second distance information indicating the distance between the resection plane 4 and the preservation region measured by the distance measurement unit 232.

The display image generation unit 234 may use graphic elements such as a color map and a color bar as the first distance information and the second distance information. The first distance information and the second distance information generated by the display image generation unit 234 are superimposed and displayed on the cross-sectional image.

FIG. 11 is a block diagram illustrating an example of a configuration of the medical image processing apparatus according to the embodiment. The medical image processing apparatus 20 includes a processor 202, a computer-readable medium 204, which is a non-transitory tangible object, a communication interface 206, and an input and output interface 208.

The medical image processing apparatus 20 may be in a form such as a server, a personal computer, a workstation, or a tablet terminal.

The processor 202 includes a central processing unit (CPU). The processor 202 may include a graphics processing unit (GPU). The processor 202 is connected to the computer-readable medium 204, the communication interface 206, and the input and output interface 208 via a bus 210. The input device 214 and the display device 216 are connected to the bus 210 via the input and output interface 208.

A keyboard, a mouse, a multi-touch panel, another pointing device, a sound input device, or the like may be used as the input device 214. Any combination of a plurality of devices may be used as the input device 214.

A liquid-crystal display, an organic EL display, a projector, or the like may be used as the display device 216. The display device 216 may use any combination of the plurality of devices. Note that EL of the organic EL display is an abbreviation for electroluminescence.

The computer-readable medium 204 includes a memory as a main storage device and a storage as an auxiliary storage device. A semiconductor memory, a hard disk device, a solid-state drive device, or the like may be used as the computer-readable medium 204. Any combination of the plurality of devices may be used as the computer-readable medium 204.

The hard disk device may be referred to as an HDD, which is an abbreviation for the English expression hard disk drive. The solid-state drive device may be referred to as an SSD, which is an abbreviation for the English expression solid-state drive.

The medical image processing apparatus 20 is connected to a communication line via the communication interface 206, and is connected to and able to communicate with devices such as a DICOM server 40 and a viewer terminal 46 connected to a medical institution network. The illustration of the communication line is omitted. DICOM is an abbreviation for digital imaging and communications in medicine.

The computer-readable medium 204 stores a plurality of programs including a medical image processing program 220 and a display control program 260. The computer-readable medium 204 stores various data, various parameters, and the like.

The processor 202 executes a command of the medical image processing program 220 to function as the image acquisition unit 222, the lesion region extraction unit 224, the lesion region input reception unit 226, the resection plane extraction unit 228, the resection plane input reception unit 230, the distance measurement unit 232, and the display image generation unit 234.

The display control program 260 generates a display signal necessary for display output to the display device 216 and performs display control of the display device 216.

<Procedure of Medical Image Processing Method>

Figure 12:
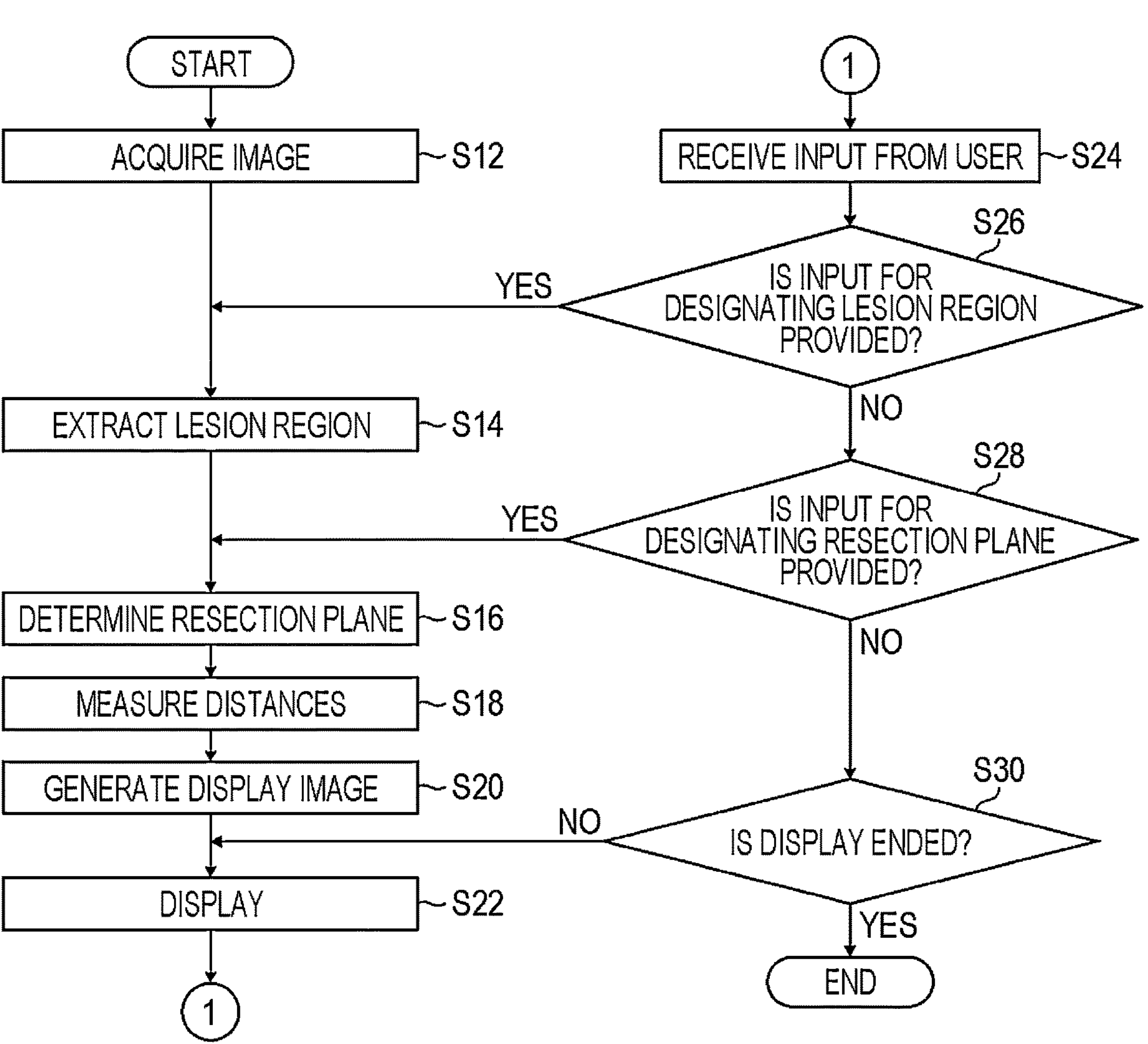
FIG. 12 is a flowchart illustrating a procedure of a medical image processing method according to the embodiment.

FIG. 12 is a flowchart illustrating a procedure of a medical image processing method according to the embodiment. In an image acquisition step S12, the processor 202 acquires a medical image to be processed from the DICOM server 40 or the like.

In a lesion region extraction step S14, the processor 202 automatically extracts a lesion region as tissue to be resected from the input medical image. In addition, in the lesion region extraction step S14, the processor 202 extracts a preservation region as tissue to be preserved from the input medical image.

Generally, in a case where a lesion is excised, the entire membrane surrounding fat around the organ in which the lesion is present is excised. In the lesion region extraction step S14, a fat region where a resection plane can be set and a membrane surrounding the fat region are extracted.

Examples of the preservation region include blood vessels, nerves, pelvises, bones, muscles, cancer, lymph nodes, ureters, and organs. The organ may be another organ other than the organ including the lesion region, or may be a region other than the lesion region in the organ including the lesion region.

The processor 202 may perform segmentation on the medical image using the trained model to extract the lesion region and the preservation region. The processor 202 can determine the lesion region and the preservation region, which have been automatically extracted, as distance measurement targets.

In a resection plane determination step S16, the processor 202 automatically extracts a candidate for the resection plane 4 based on the determined lesion region. The processor 202 may extract the membrane surrounding the fat region as a candidate for the resection plane 4. In a case where a user's input indicating the correction of the candidate for the resection plane 4 is not acquired, the processor 202 can determine the automatically extracted candidate for the resection plane 4 as the resection plane 4.

In a case where the candidate for the resection plane 4 is automatically extracted, the processor 202 may extract the candidate for the resection plane 4 in consideration of a margin designated in advance by the user. For example, in a case where 2 millimeters is designated as the margin, the outer periphery of the mesorectum may be extracted as a candidate for the resection plane 4 for a region having a CRM of 2 millimeters or more, and a surface extending 2 millimeters from the outer periphery of the cancer beyond the mesorectum may be extracted as a candidate for the resection plane 4 for a region having a CRM of less than 2 millimeters.

In a distance measurement step S18, the processor 202 measures a first distance which is the nearest neighbor distance between the resection plane 4 and the lesion region. Further, in the distance measurement step S18, the processor 202 measures a second distance which is the nearest neighbor distance between the resection plane 4 and the preservation region.

In a display image generation step S20, the processor 202 generates a display image in which first distance information indicating the first distance and second distance information indicating the second distance are superimposed and displayed on any cross-sectional image.

In a display step S22, the processor 202 displays the generated display image on the display device 216. Accordingly, the user can ascertain the distance between the resection plane 4 and the lesion region and the distance between the resection plane 4 and the preservation region in the cross-sectional image at a glance.

In the display image generation step S20, a display image representing the processing results in the lesion region extraction step S14 and the resection plane determination step S16 can be generated. In the display step S22, the display image representing the processing results in the lesion region extraction step S14 and the resection plane determination step S16 can be displayed on the display device 216.

In a user input reception step S24, the processor 202 receives an input of various instructions from the user. The user can perform various inputs such as designation of the lesion region and designation of the resection plane 4 from the input device 214.

In a lesion region designation input determination step S26, the processor 202 determines whether an input for designating a lesion region and an input for designating a preservation region have been provided from the input device 214. In a case where the user performs an operation of designating a portion suspected of a lesion in the medical image or the like, and an input of information for designating the lesion region and an input of information for designating the preservation region are provided, the determination result is YES. In a case where the determination result is YES, the processor 202 proceeds to the lesion region extraction step S14, and determines the designated lesion region and the designated preservation region as distance measurement targets.

On the other hand, in the lesion region designation input determination step S26, in a case where the processor 202 determines that no input for designating a lesion region is provided, the determination result is NO. In a case where the determination result is NO, the processor 202 proceeds to a resection plane designation step S28.

In the resection plane designation step S28, the processor 202 determines whether an input for designating the resection plane 4 has been provided from the input device 214. In a case where the user performs an operation of designating the resection plane 4 and information for designating the resection plane 4 is input, the determination result is YES. In a case where the determination result is YES, the processor 202 proceeds to the resection plane determination step S16 and determines the designated resection plane 4 as a reference for distance measurement.

On the other hand, in the resection plane designation step S28, in a case where the processor 202 determines that the information for designating the resection plane 4 is not input, the determination result is NO. In a case where the determination result is NO, the processor 202 proceeds to an end determination step S30.

In a case where the resection plane 4 is edited on the basis of an input by the user, it is preferable to perform an editing restriction that does not accept editing that does not cause a sufficient margin for the nearest neighbor distance between the resection plane 4 and the lesion region.

For example, in a case where an instruction is given for editing in which the nearest neighbor distance between the resection plane 4 and the lesion region is less than a distance designated by the user in advance, a mode in which the editing is disabled may be applied. In a case where the editing is disabled, an error message may be displayed on the display device 216.

In the end determination step S30, the processor 202 determines whether or not to end the display of the medical image. The end condition for the display may be an input of an end instruction by the user or an end instruction based on a program. In a case where the end condition is not satisfied and the determination result of the end determination step S30 is NO, the processor 202 proceeds to the display step S22 and continues the display.

On the other hand, in the end determination step S30, in a case where the end condition is satisfied, for example, the user performs an operation of closing a display window, the determination result is YES. In a case where the determination result is YES, the processor 202 ends the display and ends the flowchart of FIG. 12.

Note that the processing functions of the medical image processing apparatus 20 can also be implemented by sharing the processing using a plurality of computers.

Display Example of First Distance Information and Second Distance Information

FIG. 13 is an image diagram illustrating an example in which three-dimensional distance information is superimposed and displayed on a two-dimensional cross section. FIG. 13 illustrates a two-dimensional cross-sectional image in an arbitrary cross section. In a cross-sectional image 300 illustrated in FIG. 13, a resection line 301 is adjusted based on the designation of the doctor who is the user in a region where the cancer 5 is close to the nerve 3.

A first color map 302 indicating a distribution of the nearest neighbor distance between the resection line 301 and the cancer 5 is displayed in an outer edge region of the resection line 301 on the cancer 5 side. In addition, a second color map 304 indicating a distribution of the nearest neighbor distance between the resection line 301 and the nerve 3 is displayed in an outer edge region of the resection line 301 on the nerve 3 side.

A region in contact with the resection line 301 may be used as the outer edge region of the resection line 301. A region not in contact with the resection line 301 may be used as the outer edge region of the resection line 301.

It is preferable that the distance from the resection line 301 to the first color map 302 be equal to or less than the width of the resection line 301 or equal to or less than the width of the first color map 302. Similarly, it is preferable that the distance from the resection line 301 to the second color map 304 be equal to or less than the width of the resection line 301 or equal to or less than the width of the second color map 304.

The first color map 302 indicates the distribution of the nearest neighbor distance between the resection line 301 and the cancer 5 at each position on the resection line 301. The resection line 301 illustrated in FIG. 13 has a line width that is narrower the shorter the nearest neighbor distance between the resection line 301 and the cancer 5 is, and is wider the longer the nearest neighbor distance between the resection line 301 and the cancer 5 is. For convenience of illustration, FIG. 13 illustrates the first color map 302 having a uniform line width. The same applies to the second color map 304.

In the first color map 302, any color is given to a region where the nearest neighbor distance between the resection line 301 and the cancer 5 is equal to or less than a prescribed threshold value. A mode in which the numerical value of the nearest neighbor distance between the resection line 301 and the cancer 5 is displayed in a case where a user's input such as a mouseover or a click is acquired may be applied to the first color map 302. For convenience of illustration, the first color map 302 illustrated in FIG. 13 does not display colors.

The same applies to the second color map 304. The first color map 302 and the second color map 304 may be distinguished from each other by differentiating a color of the first color map 302 from a color of the second color map 304.

FIG. 13 illustrates a cross-sectional image 300 in which the first color map 302 and the second color map 304 are displayed for a partial region of the resection line 301. The first color map 302 and the second color map 304 may be displayed for a plurality of regions of the resection line 301.

That is, the first color map 302 may not be displayed for a region where the nearest neighbor distance between the resection line 301 and the cancer 5 exceeds a prescribed distance. Similarly, the second color map 304 may not be displayed for a region where the nearest neighbor distance between the resection line 301 and the nerve 3 exceeds a prescribed distance.

For example, at least one of the first color map 302 and the second color map 304 may be displayed for a region of the resection line 301 determined in accordance with designation by the doctor who is the user.

FIG. 14 is an image diagram illustrating another example in which three-dimensional distance information is superimposed and displayed on a two-dimensional cross section. In a cross-sectional image 310 illustrated in FIG. 14, a first color map 312 and a second color map 314 are displayed for the entire region of the resection line 301.

The same configuration as that of the first color map 302 illustrated in FIG. 13 may be used for the first color map 312 illustrated in FIG. 14. Similarly, the same configuration as that of the second color map 304 illustrated in FIG. 13 may be used for the second color map 314 illustrated in FIG. 14.

Specific Example of User Interface

Next, a specific example of a user interface will be described. The display device 216 illustrated in FIG. 10 displays a cross-sectional image representing a result of processing performed in each step illustrated in FIG. 12.

In the lesion region extraction step S14, the display device 216 displays a result of the segmentation of the lesion region and the preservation region. For example, the display device 216 displays the cross-sectional image illustrated in FIG. 5 as the processing result of the lesion region extraction step S14.

In the resection plane determination step S16, the display device 216 displays, as candidates for the resection line, the resection line 4A illustrated in FIG. 7, the resection line 4B illustrated in FIG. 8, the resection line 4C illustrated in FIG. 9, and the like superimposed on the cross-sectional image illustrated in FIG. 5. The display device 216 may display the resection line 4C illustrated in FIG. 9 as the determined resection line.

Figure 15:
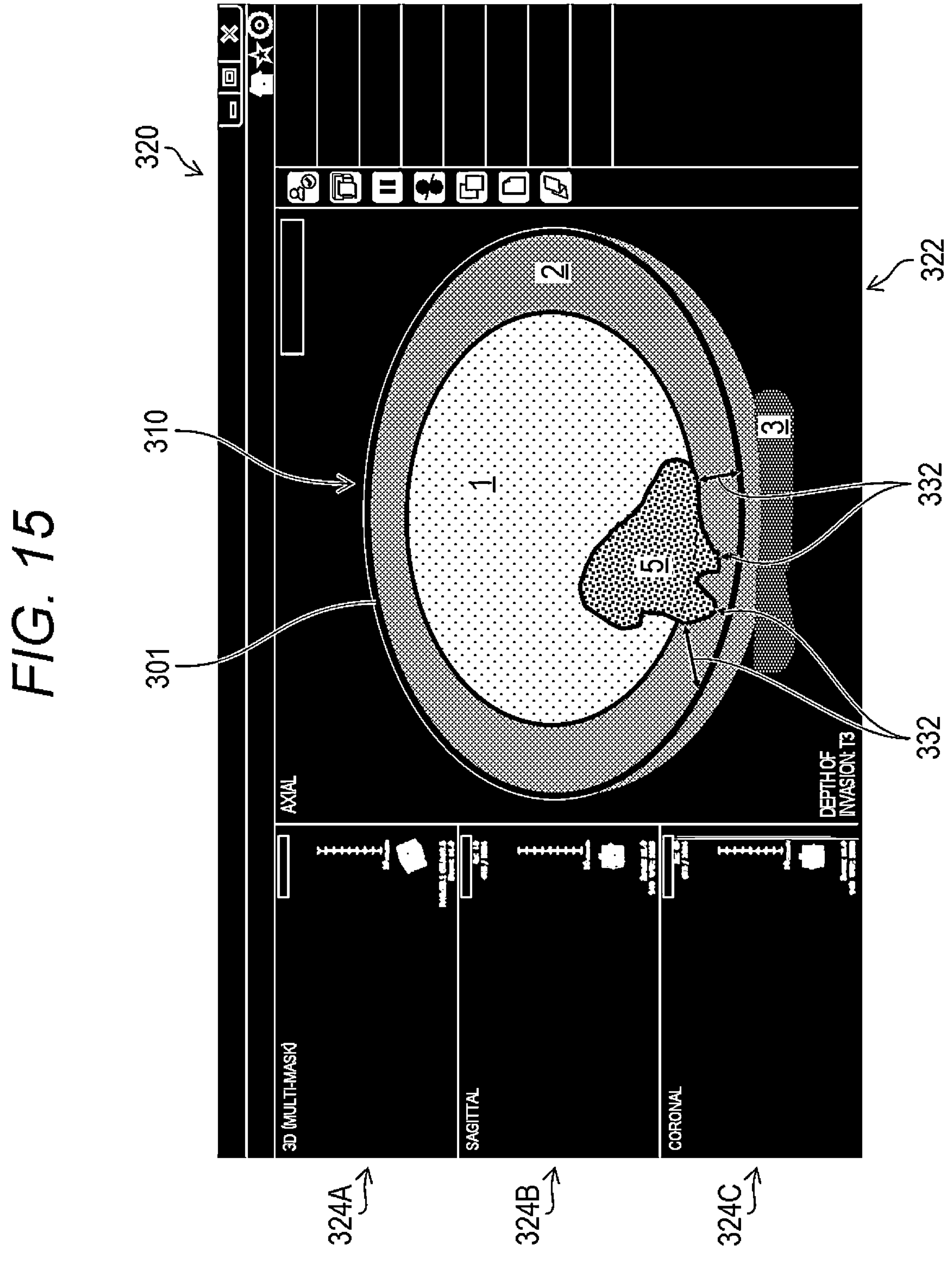
FIG. 15 is a schematic diagram illustrating an example of a display screen for a first distance measurement in a distance measurement step.

FIG. 15 is a schematic diagram illustrating an example of a display screen for a first distance measurement in the distance measurement step. A display window 320 illustrated in FIG. 15 is an example of a display form in the distance measurement step S18. The display window 320 may also be used in a case where the processing results in the lesion region extraction step S14 and the resection plane determination step S16 are displayed.

The display window 320 illustrated in FIG. 15 includes a main display area 322, a first sub-display area 324A, a second sub-display area 324B, and a third sub-display area 324C. The main display area 322 is disposed at the center of the display window 320.

The first sub-display area 324A, the second sub-display area 324B, and the third sub-display area 324C are disposed on the left side of the main display area 322 in FIG. 15. The first sub-display area 324A, the second sub-display area 324B, and the third sub-display area 324C are arranged in a vertical direction in FIG. 15.

In FIG. 15, an axial cross-sectional image is displayed in the main display area 322, and an arrow line 332 indicating the distance between any position on the resection line 301 and the cancer 5 is superimposed and displayed on the axial cross-sectional image. Instead of the arrow line 332, a numerical value may be displayed.

FIG. 15 illustrates the cross-sectional image 310 illustrated in FIG. 14 as the axial cross-sectional image. The same applies to axial cross-sectional images in FIGS. 16 to 19.

Figure 16:
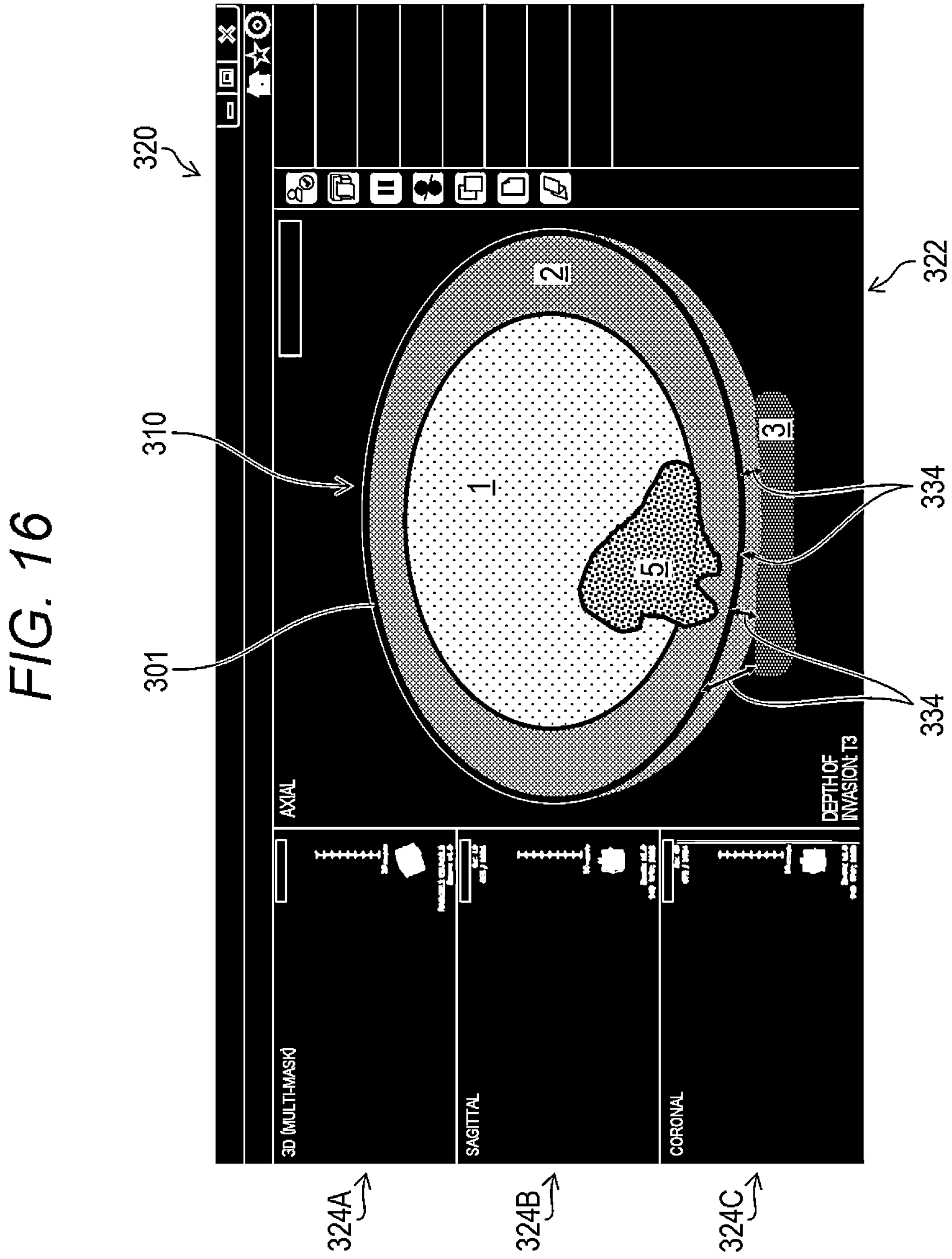
FIG. 16 is a schematic diagram illustrating an example of a display screen for a second distance measurement in the distance measurement step.

FIG. 16 is a schematic diagram illustrating an example of a display screen for a second distance measurement in the distance measurement step. FIG. 16 illustrates an example in which an arrow line 334 indicating the distance between the resection line 301 and the nerve 3 is displayed. The arrow line 332 illustrated in FIG. 15 and the arrow line 334 illustrated in FIG. 16 may be displayed on the same display screen.

The arrow line 332 illustrated in FIG. 15 and the arrow line 334 illustrated in FIG. 16 may be displayed for all distance measurement positions, or may be displayed for some distance measurement positions such as representative measurement positions.

Figure 17:
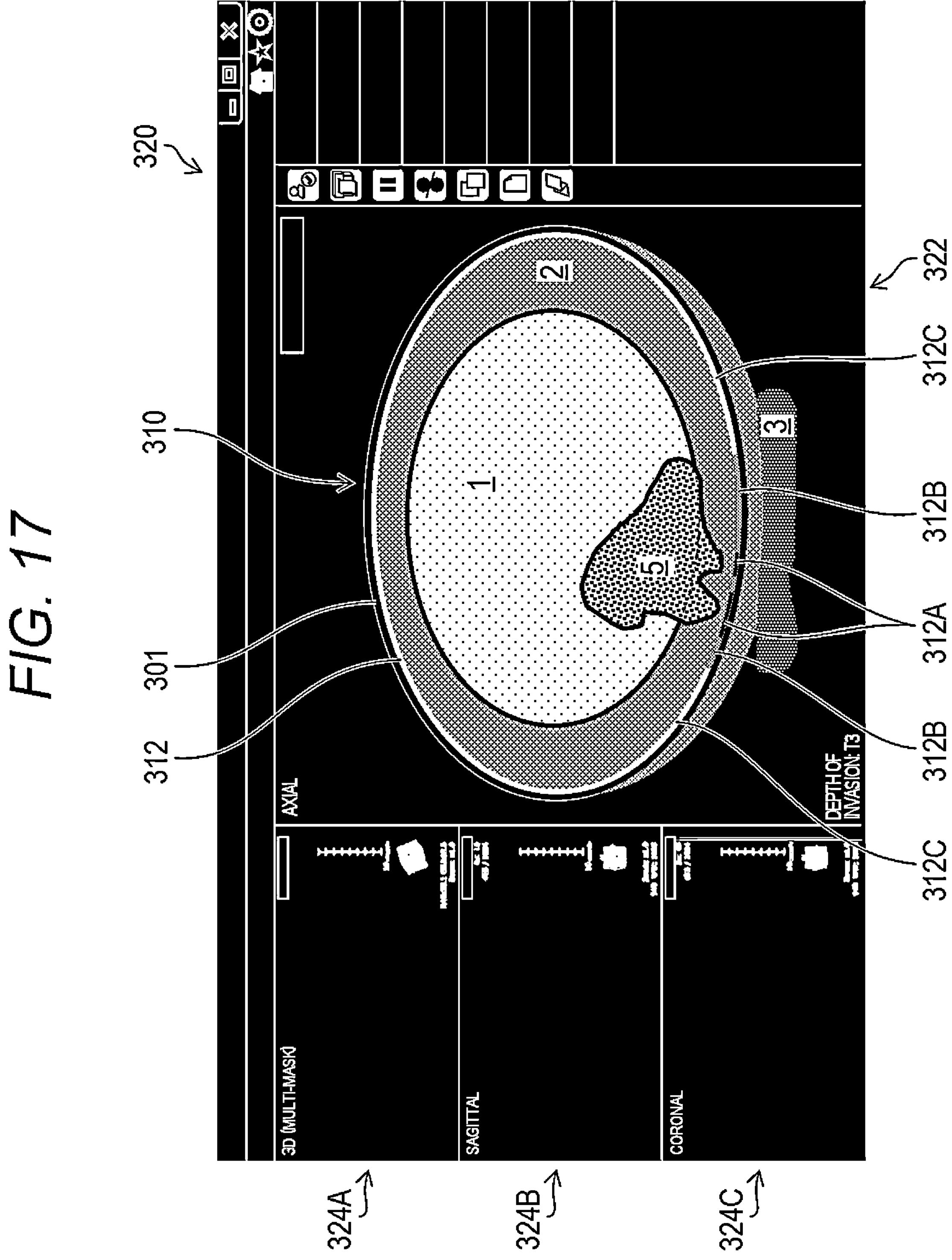
FIG. 17 is a schematic diagram illustrating a display example of a first color map.

FIG. 17 is a schematic diagram illustrating a display example of the first color map. FIG. 17 illustrates the first color map 312 illustrated in FIG. 14. The first color map 312 illustrated in FIG. 17 uses both the display of the nearest neighbor distance using a line width and the display of the nearest neighbor distance using a color. That is, the first color map 312 has a density according to the nearest neighbor distance between the resection line 301 and the cancer 5, that is, has a high density in a case where the nearest neighbor distance between the resection line 301 and the cancer 5 is relatively short, and has a low density in a case where the nearest neighbor distance between the resection line 301 and the cancer 5 is relatively long.

For example, a first color region 312A in the first color map 312 has a higher density than those of a second color region 312B and a third color region 312C, and the distance between the resection line 301 and the cancer 5 around the first color region 312A is shorter than those around the second color region 312B and the third color region 312C.

Although the first color map 312 illustrated in FIG. 17 indicates stepwise changes in the nearest neighbor distance between the resection line 301 and the cancer 5, a first color map indicating continuous changes in the nearest neighbor distance between the resection line 301 and the cancer 5 may be used.

The first color map 312 illustrated in FIG. 17 represents a variation in the nearest neighbor distance between the resection line 301 and the cancer 5 by using a difference in density, but may represent a variation in the nearest neighbor distance between the resection line 301 and the cancer 5 by using a difference in color, a difference in saturation of the same color, or a difference in brightness of the same color. The same applies to the second color map 314 illustrated in FIG. 18.

Figure 18:
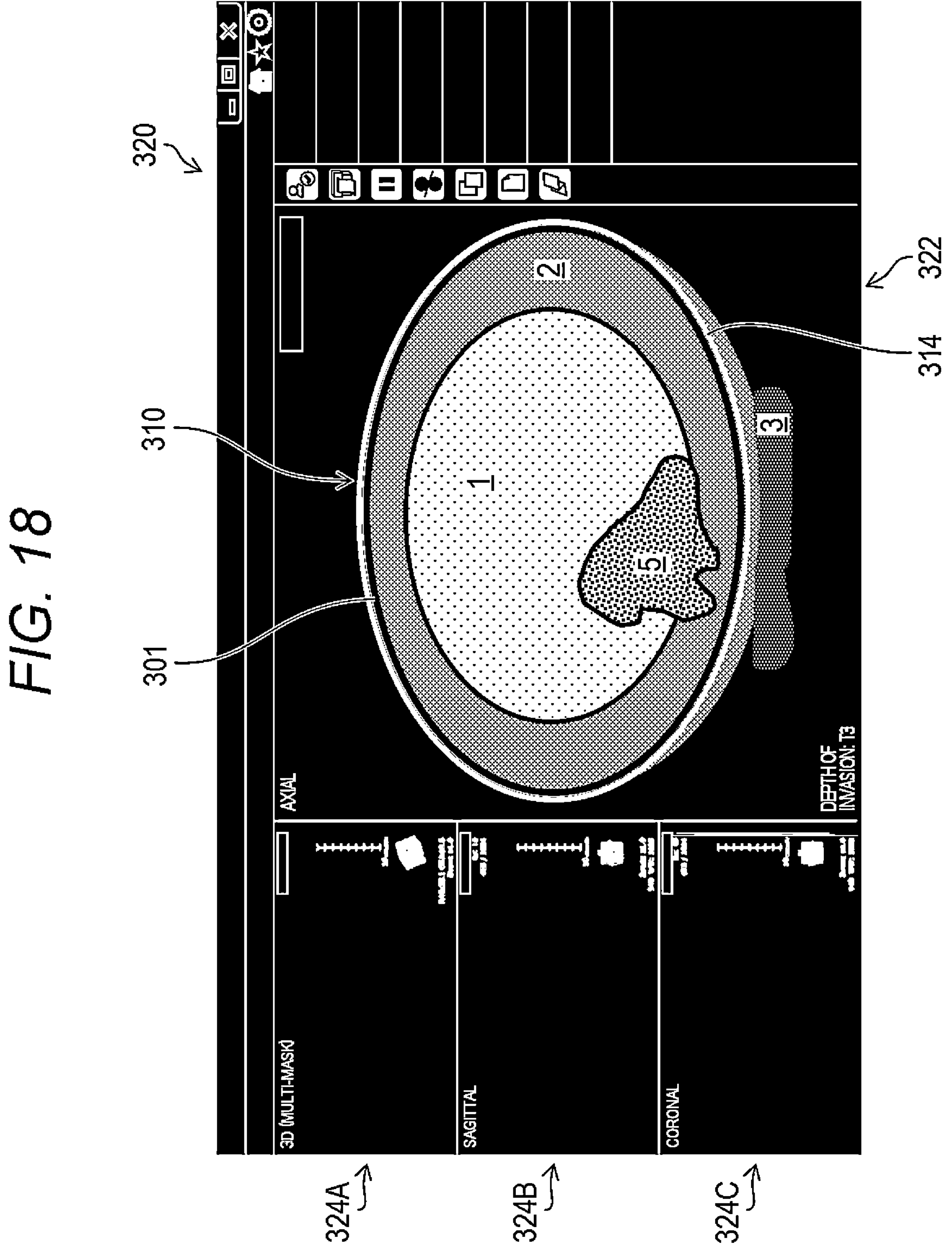
FIG. 18 is a schematic diagram illustrating a display example of a second color map.

FIG. 18 is a schematic diagram illustrating a display example of the second color map. FIG. 18 illustrates the second color map 314 illustrated in FIG. 14. The second color map 314 is configured in the same manner as the first color map 312 illustrated in FIG. 17. Here, the detailed description of the second color map 314 is omitted.

Figure 19:
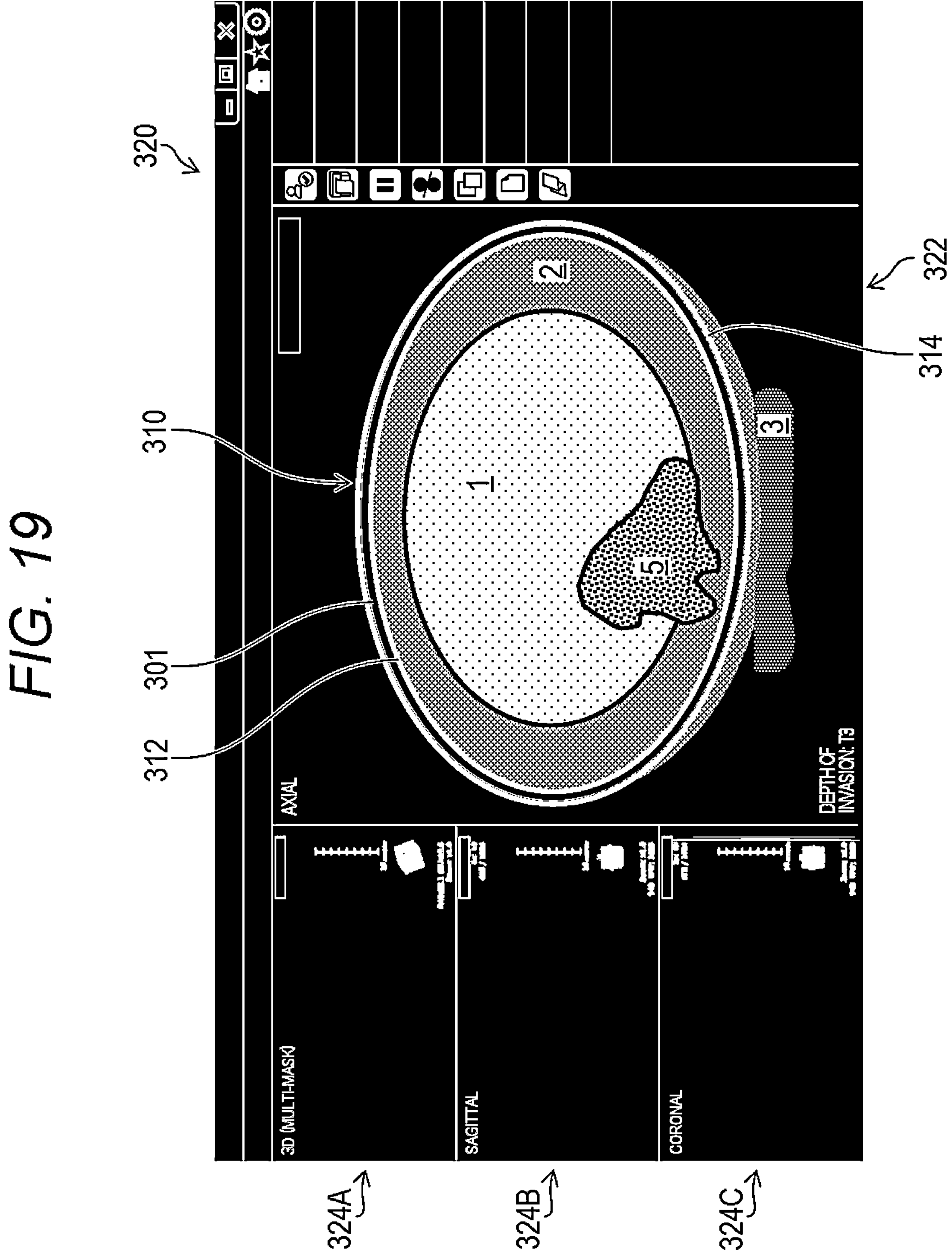
FIG. 19 is a schematic diagram illustrating a display example of a color map according to a modification.

FIG. 19 is a schematic diagram illustrating a display example of a color map according to a modification. FIG. 19 illustrates an example in which the first color map 312 and the second color map 314 are superimposed and displayed on the cross-sectional image 310.

Either the first color map 312 or the second color map 314 may be selectively superimposed and displayed on the cross-sectional image 310. A mode in which only the first color map 312 is displayed, a mode in which only the second color map 314 is displayed, and a mode in which both the first color map 312 and the second color map 314 are displayed may be selectively switched according to an input by the user.

FIGS. 15 to 19 illustrate a mode in which the first color map 312 and the second color map 314 illustrated in FIG. 14 are displayed, but the first color map 302 and the second color map 304 illustrated in FIG. 13 may be displayed.

Example of Application to Volume Rendering Image

Similarly to the cross-sectional image 300 and the like illustrated in FIG. 13, the first distance information corresponding to the first color map 302 and the second distance information corresponding to the second color map 304 illustrated in FIG. 13 and the like can be superimposed and displayed on a volume rendering image.

The display image generation unit 234 illustrated in FIG. 10 may generate a volume rendering image from a group of a plurality of cross-sectional images. The display image generation unit 234 can generate a plurality of volume rendering images viewed from different viewpoints of the user. The display image generation unit 234 can generate a color map corresponding to the volume rendering image.

Figure 20:
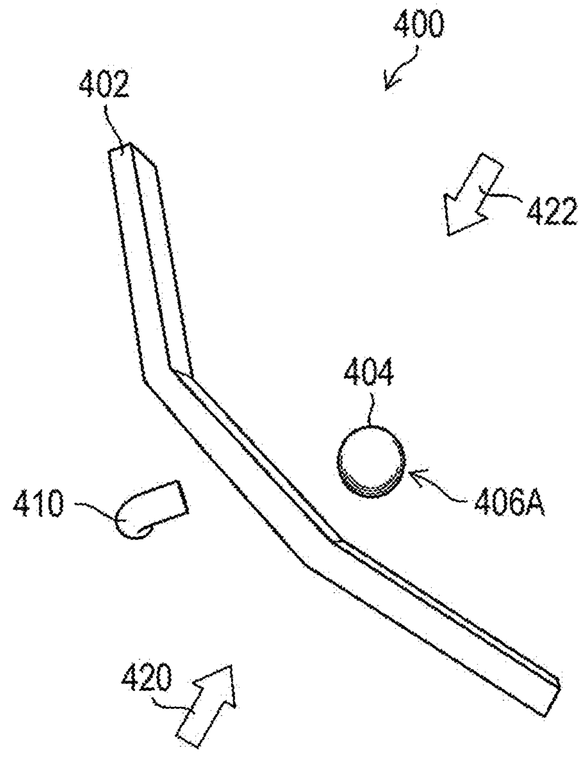
FIG. 20 is a schematic diagram illustrating a display example of three-dimensional distance information in a volume rendering image.

FIG. 20 is a schematic diagram illustrating a display example of three-dimensional distance information in a volume rendering image. FIG. 20 illustrates a volume rendering image 400 in which a resection plane 402, a tumor 404 which is tissue to be resected, and a blood vessel 410 which is tissue to be preserved are viewed from above.

Note that an arrow line 420 indicates the direction of a viewpoint in a case where the resection plane 402 is viewed from the blood vessel 410 side. An arrow line 422 indicates the direction of a viewpoint in a case where the resection plane 402 is viewed from the tumor 404 side.

At the tumor 404, a first color map 406A is superimposed and displayed at a position facing the resection plane 402. The first color map 406A represents information of the nearest neighbor distance between the resection plane 402 and the tumor 404. The first color map 406A is used in the volume rendering image in a case where the resection plane 402 is viewed from the tumor 404 side.

Figure 21:
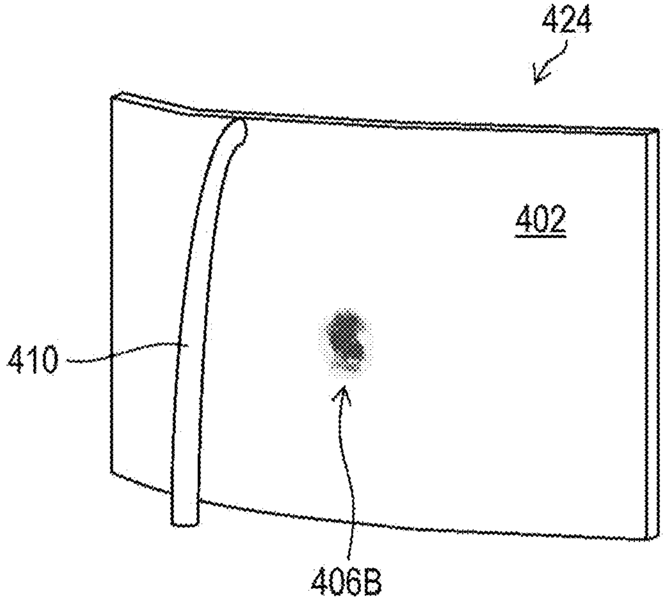
FIG. 21 is a schematic diagram of the three-dimensional distance information illustrated in FIG. 20 as viewed from the side on which tissue to be preserved is displayed.

FIG. 21 is a schematic diagram of the three-dimensional distance information illustrated in FIG. 20 as viewed from the side on which the tissue to be preserved is displayed. In a volume rendering image 424 illustrated in FIG. 21, a first color map 406B is displayed on a surface of the resection plane 402 on the blood vessel 410 side.

The position of the first color map 406B on the resection plane 402 corresponds to the position of the tumor 404 in a case where the tumor 404 is projected onto the resection plane 402. The position of the center of mass of the tumor 404 may be used as the position of the tumor 404. The shape of the first color map 406B corresponds to the shape of the tumor 404 in a case where the tumor 404 is projected onto the resection plane 402.

The first color map 406B indicates the nearest neighbor distance between the resection plane 402 and the tumor 404 that is on the opposite side of the blood vessel 410 with respect to the resection plane 402 and that is not visually recognized in the volume rendering image 424. A color that can be distinguished from the resection plane 402 and the blood vessel 410 is used for the first color map 406B.

A density corresponding to the nearest neighbor distance between the tumor 404 and the resection plane 402 is used in the first color map 406B. For example, in a case where the nearest neighbor distance between the tumor 404 and the resection plane 402 is relatively short, the density of the first color map 406B is relatively high.

A second color map indicating the nearest neighbor distance between the resection plane 402 and the blood vessel 410 may be superimposed and displayed on the volume rendering image 424. In FIG. 21, the illustration of the second color map is omitted.

Figure 22:
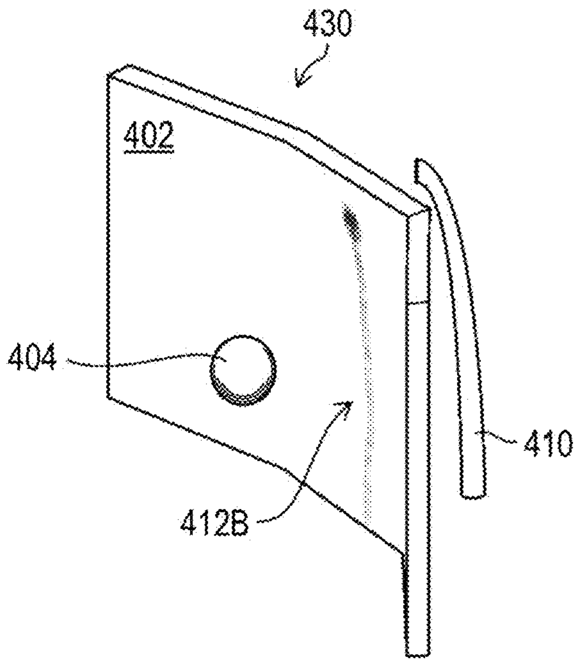
FIG. 22 is a schematic diagram of the three-dimensional information illustrated in FIG. 20 as viewed from the side on which tissue to be resected is displayed.

FIG. 22 is a schematic diagram of the three-dimensional information illustrated in FIG. 20 as viewed from the side on which the tissue to be resected is displayed. In a volume rendering image 430 illustrated in FIG. 22, a second color map 412B is superimposed and displayed on the surface of the resection plane 402 on the side on which the tumor 404 is displayed.

The second color map 412B indicates the nearest neighbor distance between the resection plane 402 and the blood vessel 410 that is on the opposite side of the tumor 404 with respect to the resection plane 402 and that is not visually recognized in the volume rendering image 430. A color that can be distinguished from the resection plane 402 and the tumor 404 is used for the first color map 406B.

A first color map indicating the nearest neighbor distance between the resection plane 402 and the tumor 404 may be superimposed and displayed on the volume rendering image 430. In FIG. 22, the illustration of the first color map is omitted.

The position and shape of the second color map 412B on the resection plane 402 and the display form of the nearest neighbor distance between the resection plane 402 and the blood vessel 410 are the same as the position and shape of the first color map 406B illustrated in FIG. 21 and the display form of the nearest neighbor distance between the resection plane 402 and the blood vessel 410 illustrated in FIG. 21.

Figure 23:
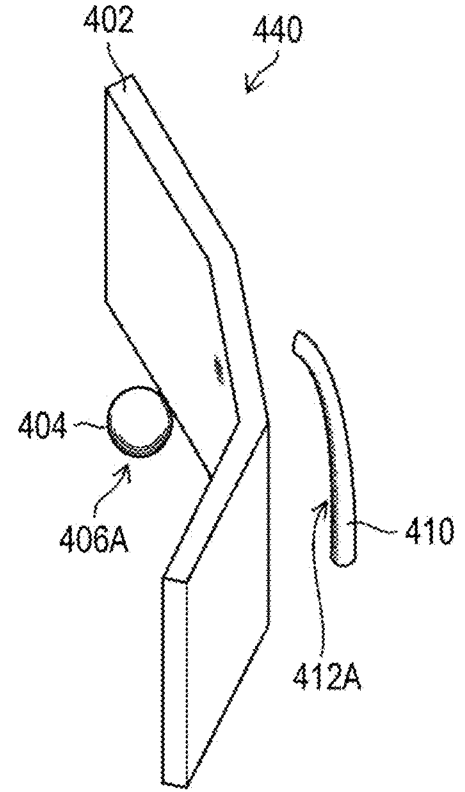
FIG. 23 is a schematic diagram illustrating a display example of three-dimensional distance information used for tissue illustrated in FIG. 20.

FIG. 23 is a schematic diagram illustrating a display example of three-dimensional distance information used for the tissue illustrated in FIG. 20. A first color map 406A representing the nearest neighbor distance between the resection plane 402 and the tumor 404 and a second color map 412A representing the nearest neighbor distance between the resection plane 402 and the blood vessel 410 are superimposed and displayed on a volume rendering image 440 illustrated in FIG. 23.

The first color map 406A is displayed on tissue between the resection plane 402 and the tumor 404, while the tissue is on the tumor 404 side with respect to the resection plane 402. The second color map 412A is displayed on tissue between the resection plane 402 and the blood vessel 410, while the tissue is on the blood vessel 410 side with respect to the resection plane 402.

That is, in the volume rendering image viewed from the viewpoint on the side on which the tissue to be preserved is displayed, in a case where the tissue to be resected is on the opposite side of the viewpoint with respect to the resection plane and cannot be seen, the first color map is displayed on the resection plane. The second color map is displayed on the tissue between the resection plane and the tissue to be preserved.

Similarly, in the volume rendering image viewed from the viewpoint on the side on which the tissue to be resected is displayed, in a case where the tissue to be preserved is on the opposite side of the viewpoint with respect to the resection plane and cannot be seen, the second color map is displayed on the resection plane. Further, the first color map is displayed on the tissue between the resection plane and the tissue to be preserved.

Example of Application to Medical Information System

Figure 24:
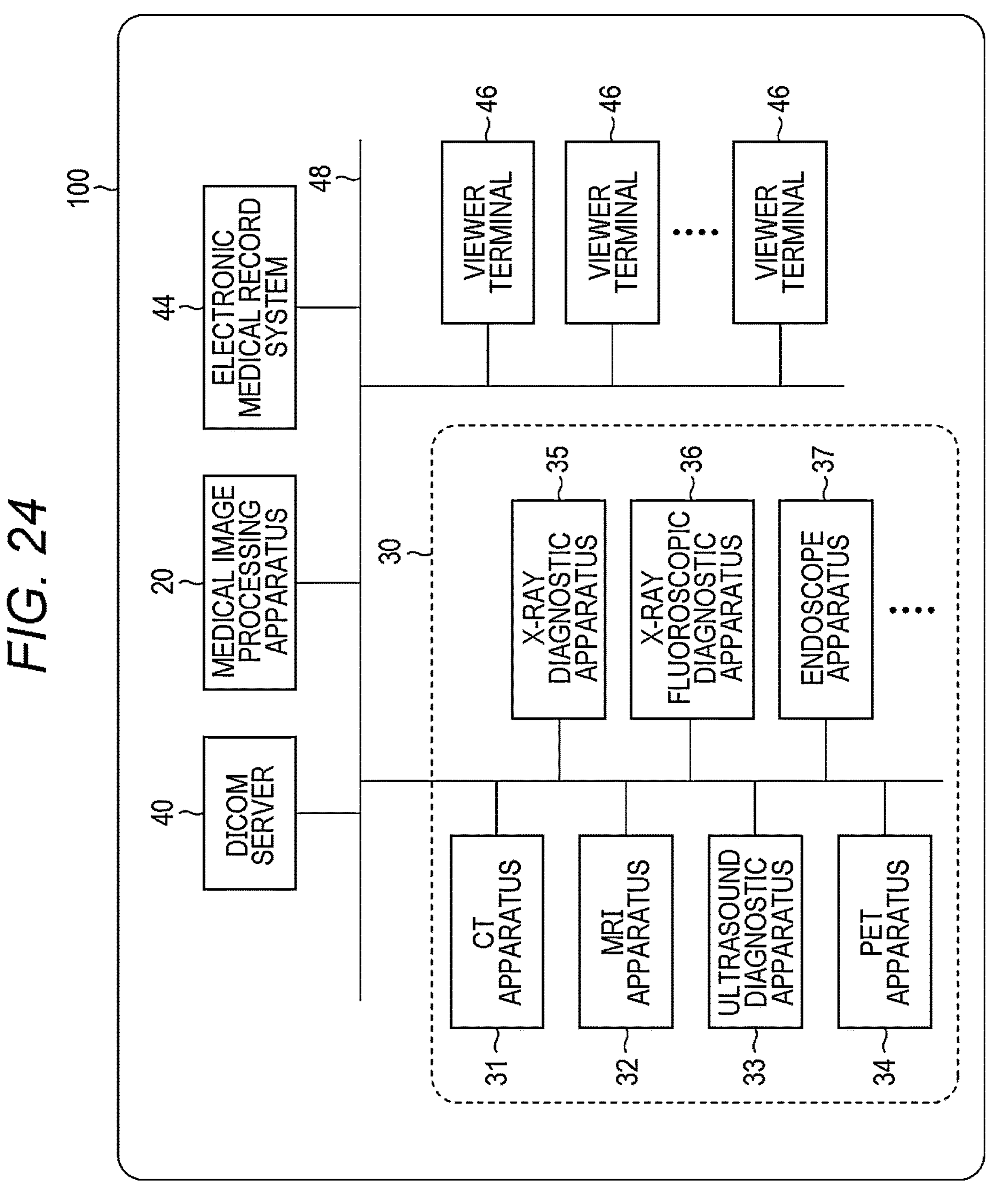
FIG. 24 is a block diagram illustrating an example of a configuration of a medical information system including the medical image processing apparatus according to the embodiment.

FIG. 24 is a block diagram illustrating an example of a configuration of a medical information system including the medical image processing apparatus according to the embodiment. A medical information system 100 is a computer network constructed in a medical institution such as a hospital.

The medical information system 100 includes a modality 30 that captures a medical image, the DICOM server 40, the medical image processing apparatus 20, an electronic medical record system 44, and the viewer terminal 46. The components of the medical information system 100 are connected to each other via a communication line 48. The communication line 48 may be a private communication line within the medical institution. A part of the communication line 48 may be a wide area communication line.

Examples of the modality 30 include a CT apparatus 31, an MRI apparatus 32, an ultrasound diagnostic apparatus 33, a PET apparatus 34, an X-ray diagnostic apparatus 35, an X-ray fluoroscopic diagnostic apparatus 36, and an endoscope apparatus 37. There may be various combinations of the types of modalities 30 connected to the communication line 48 for each medical institution. PET is an abbreviation for positron emission tomography.

The DICOM server 40 is a server that operates according to the DICOM specifications. The DICOM server 40 is a computer that stores and manages various kinds of data including an image captured using the modality 30, and includes a large-capacity external storage device and a database management program.

The DICOM server 40 communicates with other apparatuses via the communication line 48 to transmit and receive various kinds of data including image data. The DICOM server 40 receives various kinds of data including image data generated by using the modality 30 via the communication line 48, and stores and manages the data in a recording medium such as the large-capacity external storage device. The storage format of the image data and the communication between the apparatuses via the communication line 48 are based on the DICOM protocol.

The medical image processing apparatus 20 can acquire data from the DICOM server 40 and the like via the communication line 48. The medical image processing apparatus 20 can transmit the processing results to the DICOM server 40 and the viewer terminal 46. The processing functions of the medical image processing apparatus 20 may be installed on the DICOM server 40 or may be installed on the viewer terminal 46.

Various kinds of information including various kinds of data stored in a database of the DICOM server 40 and the processing results generated by the medical image processing apparatus 20 can be displayed on the viewer terminal 46.

The viewer terminal 46 is an image viewing terminal called a PACS viewer or a DICOM viewer. A plurality of viewer terminals 46 may be connected to the communication line 48. The form of the viewer terminal 46 is not particularly limited, and the viewer terminal 46 may be a personal computer, a workstation, or a tablet terminal. An input device of the viewer terminal 46 may be configured to be able to designate a lesion region, a measurement reference plane, and the like.

Example of Application to Program for Operating Computer

A program for causing a computer to implement the processing functions in the medical image processing apparatus 20 can be stored in a computer-readable medium that is a tangible non-transitory information storage medium such as an optical disc, a magnetic disk, or a semiconductor memory, and the program can be provided through the information storage medium.

Instead of a mode in which the program is stored in such a tangible non-transitory computer-readable medium and provided, a program signal may be provided as a download service using an electric telecommunication line, such as the Internet.

<Regarding Hardware Configuration of Each Processing Unit>

The hardware structures of the processing units that execute various kinds of processing, such as the image acquisition unit 222, the lesion region extraction unit 224, the lesion region input reception unit 226, the resection plane extraction unit 228, the resection plane input reception unit 230, the distance measurement unit 232, and the display image generation unit 234 in the medical image processing apparatus 20, are, for example, various processors as described below. Note that each of the processing units may include an aspect called a processing unit. The processor may be referred to as the English expression processor.

The various processors include a CPU which is a general-purpose processor that executes a program to function as the various processing units, a GPU which is a processor specialized in image processing, a programmable logic device such as an FPGA which is a processor having a circuit configuration that can be changed after manufacture, and a dedicated electric circuit such as an ASIC which is a processor having a circuit configuration exclusively designed to execute specific processing.

Note that FPGA is an abbreviation for field-programmable gate array. ASIC is an abbreviation for application-specific integrated circuit. The programmable logic device may be referred to as a PLD, which is an abbreviation for the English expression programmable logic device.

Each of the processing units may be configured by one of these various processors, or may be configured by two or more processors of the same type or different types among the various processors. For example, each of the processing units may be configured by a plurality of FPGAs, a combination of a CPU and an FPGA, or a combination of a CPU and a GPU. A plurality of processing units may be constituted by a single processor. As an example of configuring a plurality of processing units via one processor, first, as represented by a computer such as a client and a server, there is a form in which one processor is configured by a combination of one or more CPUs and software, and this processor functions as a plurality of processing units. Second, as represented by a system-on-chip or the like, there is a form in which a processor is used that implements the functions of the entire system including a plurality of processing units with one IC chip. As described above, the various processing units are configured using one or more of the various processors as a hardware structure.

The system-on-chip may be referred to as an SoC, which is an abbreviation for the English expression system-on-chip. IC is an abbreviation for integrated circuit.

More specifically, each of the hardware structures of these various processors is an electric circuit in which circuit elements such as semiconductor elements are combined. The electric circuit may be referred to as the English expression circuitry.

Operational Effects of Medical Image Processing Apparatus According to Embodiment The medical image processing apparatus 20 according to the embodiment obtains the following operational effects.

[1]

In a case where tissue to be resected, such as a lesion region, is resected, a resection plane between the tissue to be resected and tissue to be preserved is designated, and the nearest neighbor distance between the resection plane and the tissue to be resected and the nearest neighbor distance between the resection plane and the tissue to be preserved are measured. Based on the measurement results, first distance information indicating information of the nearest neighbor distance between the resection plane and the tissue to be resected and second distance information indicating information of the nearest neighbor distance between the resection plane and the tissue to be preserved are superimposed and displayed on a two-dimensional cross-sectional image. Accordingly, it is possible to support the determination of the resection plane in a case where the tissue to be resected is resected.

[2]

The first distance information displayed on the cross-sectional image is displayed in an outer edge region of the resection plane on the side on which the tissue to be resected is displayed with respect to the resection plane. Accordingly, a decrease in the visibility of the resection plane is suppressed, and the visibility of the first distance information and the side on which the first distance is applied can be ascertained at a glance.

[3]

The second distance information displayed on the cross-sectional image is displayed in an outer edge region of the resection plane on the side on which the tissue to be preserved is displayed with respect to the resection plane. Accordingly, a decrease in the visibility of the resection plane is suppressed, and the visibility of the second distance information and the side on which the second distance is applied can be ascertained at a glance.

[4]

The first distance information displayed in a volume rendering image is displayed on the side on which the tissue to be preserved is displayed with respect to the resection plane. Accordingly, the first distance information corresponding to the tissue hidden by the resection plane and to be resected can be visually recognized.

[5]

The second distance information displayed in the volume rendering image is displayed on the side on which the tissue to be resected is displayed with respect to the resection plane. Accordingly, the second distance information corresponding to the tissue hidden by the resection plane and to be preserved can be visually recognized.

[6]

A color map is used as the first distance information and the second distance information. Accordingly, the user who sees the first distance information and the second distance information can ascertain the content of the first distance information at a glance.

In the embodiments of the present invention described above, constituent elements can be appropriately changed, added, or deleted without departing from the scope of the present invention. The present invention is not limited to the embodiments described above, and many modifications can be made by those skilled in the art within the technical idea of the present invention. In addition, the embodiments, the modifications, and the application examples may be appropriately combined and implemented.

Explanation of References

1: Rectum
2: Fat
3: Nerve
4: Resection plane
4A: Resection line
4B: Resection line
4C: Resection line
5: Cancer
6: Boundary
7: Region
20: Medical image processing apparatus
30: Modality
31: CT apparatus
32: MRI apparatus
33: Ultrasound diagnostic apparatus
34: PET apparatus
35: X-ray diagnostic apparatus
36: X-ray fluoroscopic diagnostic apparatus
37: Endoscope apparatus
40: DICOM server
44: Electronic medical record system
46: Viewer terminal
48: Communication line
100: Medical information system
202: Processor
204: Computer-readable medium
206: Communication interface
208: Input and output interface
210: Bus
214: Input device
216: Display device
220: Medical image processing program
222: Image acquisition unit
224: Lesion region extraction unit
226: Lesion region input reception unit
228: Resection plane extraction unit
230: Resection plane input reception unit
232: Distance measurement unit
234: Display image generation unit
260: Display control program
300: Cross-sectional image
302: First color map
304: Second color map
310: Cross-sectional image
312: First color map
312A: First color region
312B: Second color region

312C: Third color region
314: Second color map
320: Display window
322: Main display area
324A: First sub-display area
324B: Second sub-display area
324C: Third sub-display area
332: Arrow line
334: Arrow line
402: Resection plane
404: Tumor
406A: First color map
406B: First color map
410: Blood vessel
412A: Second color map
412B: Second color map
420: Arrow line
422: Arrow line
424: Volume rendering image
430: Volume rendering image
440: Volume rendering image
ME: Mesorectum
MP: Muscularis propria
TU: Cancer
S12 to S30: Steps of medical image processing method

What is claimed is:

1. A medical image processing apparatus comprising:

a processor; and a storage device in which a program executed using the processor is stored, wherein the processor is configured to execute a command of the program to acquire a three-dimensional medical image, set a separation plane for separating a first region specified in the medical image, measure a first distance which is a nearest neighbor distance between any position on a surface of the first region and the separation plane, measure a second distance which is a nearest neighbor distance between any position on a surface of a second region specified in the medical image and the separation plane, and display at least one of first distance information indicating the first distance or second distance information indicating the second distance in a case where the medical image is displayed on a display device, wherein the first distance is between a first point on the surface of the first region and a first correspondence point on the separation plane, wherein the second distance is between a second point on the surface of the second region and a second correspondence point on the separation plane, and wherein the processor is further configured to display a resection line comprising the first correspondence point and the second correspondence point along with at least one of the first distance information or the second distance information on the display.

2. The medical image processing apparatus according to claim 1, wherein the processor is configured to execute a command of the program to display the first distance information in an outer edge region of the separation plane on a first region side in a case where a cross-sectional image corresponding to an arbitrary cross section in the medical image is displayed on the display device.

3. The medical image processing apparatus according to claim 1, wherein the processor is configured to execute a command of the program to display the second distance information in an outer edge region of the separation plane on a second region side in a case where a cross-sectional image corresponding to an arbitrary cross section in the medical image is displayed on the display device.

4. The medical image processing apparatus according to claim 1, wherein the processor is configured to execute a command of the program to display the first distance information and the second distance information by applying a color map representing a distance using a color.

5. The medical image processing apparatus according to claim 1, wherein the processor is configured to execute a command of the program to display a volume rendering image corresponding to the medical image on the display device, and display at least one of the first distance information or the second distance information superimposed on the volume rendering image.

6. The medical image processing apparatus according to claim 5, wherein the processor is configured to execute a command of the program to change a display form of the first distance information and a display form of the second distance information according to a user's viewpoint in the volume rendering image.

7. The medical image processing apparatus according to claim 6, wherein the processor is configured to execute a command of the program to display the first distance information superimposed on the first region in a case where the first region is present on the user's viewpoint side of the separation plane in the volume rendering image.

8. The medical image processing apparatus according to claim 6, wherein the processor is configured to execute a command of the program to display the second distance information superimposed on the separation plane in a case where the second region is present on an opposite side of the user's viewpoint with respect to the separation plane in the volume rendering image.

9. The medical image processing apparatus according to claim 6, wherein the processor is configured to execute a command of the program to display the first distance information superimposed on the separation plane in a case where the first region is present on an opposite side of the user's viewpoint with respect to the separation plane in the volume rendering image.

10. The medical image processing apparatus according to claim 6, wherein the processor is configured to execute a command of the program to display the second distance information superimposed on the second region in a case where the second region is present on the user's viewpoint side of the separation plane in the volume rendering image.

11. A medical image processing method comprising, via a computer:

acquiring a three-dimensional medical image;

setting a separation plane for separating a first region specified in the medical image;

measuring a first distance which is a nearest neighbor distance between any position on a surface of the first region and the separation plane;

measuring a second distance which is a nearest neighbor distance between any position on a surface of a second region specified in the medical image and the separation plane;

displaying at least one of first distance information indicating the first distance or second distance information indicating the second distance in a case where the medical image is displayed on a display device, wherein the first distance is between a first point on the surface of the first region and a first correspondence point on the separation plane, wherein the second distance is between a second point on the surface of the second region and a second correspondence point on the separation plane; and displaying a resection line comprising the first correspondence point and the second correspondence point along with at least one of the first distance information or the second distance information on the display.

12. A non-transitory, computer-readable tangible recording medium in which a program for causing, when read by a computer, the computer to execute the medical image processing method according to claim 11 is recorded.

13. The medical image processing apparatus according to claim 1, wherein the first region is a lesion region, wherein the second region is a peripheral organ of the lesion region, and wherein the separation plane is a resection plane.

* * * * *